United States Patent [19]

Kimoto et al.

[11] Patent Number: 4,555,369
[45] Date of Patent: Nov. 26, 1985

[54] FLUORINATED ETHER ACYL FLUORIDES HAVING ALKYLTHIO OR ALKYLSULFONE GROUPS

[75] Inventors: Kyoji Kimoto, Kanagawa; Hirotsugu Miyauchi, Tokyo; Jukichi Ohmura, Kanagawa; Mikio Ebisawa, Kanagawa; Toshioki Hane, Kanagawa, all of Japan

[73] Assignee: Asahi Kasei Kogyo Kabushiki Kaisha, Osaka, Japan

[21] Appl. No.: 527,425

[22] Filed: Aug. 29, 1983

Related U.S. Application Data

[62] Division of Ser. No. 299,164, Sep. 3, 1981, Pat. No. 4,510,328, which is a division of Ser. No. 152,847, May 23, 1980, Pat. No. 4,329,434.

[30] Foreign Application Priority Data

May 31, 1979 [JP] Japan .................................. 54-67888
May 31, 1979 [JP] Japan .................................. 54-67889
Jul. 9, 1979 [JP] Japan .................................. 54-85852
Jul. 18, 1979 [JP] Japan .................................. 54-90301
Jul. 18, 1979 [JP] Japan .................................. 54-90302

[51] Int. Cl.$^4$ ............................................. C07C 53/50
[52] U.S. Cl. .................................................. 260/544 F
[58] Field of Search ........... 260/544 F, 543 H, 543 R, 260/513 F

[56] References Cited

U.S. PATENT DOCUMENTS 3,301,893  1/1967  Putnam et al. .................. 260/513 F Primary Examiner—Natalie Trousof
Assistant Examiner—L. Hendriksen
Attorney, Agent, or Firm—Birch, Stewart, Kolasch & Birch

[57] ABSTRACT

A novel fluorinated cation exchange membrane containing carboxylic acid groups and sulfonic acid groups, both in the form of a specific pendant structure, the carboxylic acid groups being at least 20% on one surface of the membrane and gradually decreasing toward the innerside of the membrane, which membrane is useful in electrolysis of an aqueous alkali metal halide solution with advantageously stable performance for a long term under more severe operational conditions than those conventionally used. The membrane can be prepared from a novel copolymer of a fluorinated olefin with a novel sulfur containing fluorinated vinylether of the formula:

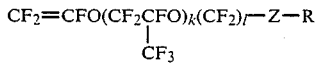

wherein k is 0 or 1, l is an integer of 3 to 5, Z is —S— or —SO$_2$— and R is C$_1$-C$_{10}$ alkyl, an aryl, Cl or C$_1$-C$_{10}$ perfluoroalkyl. Acyl fluorides, which are the precursors of the fluorinated olefin ethers, are also disclosed.

5 Claims, 1 Drawing Figure

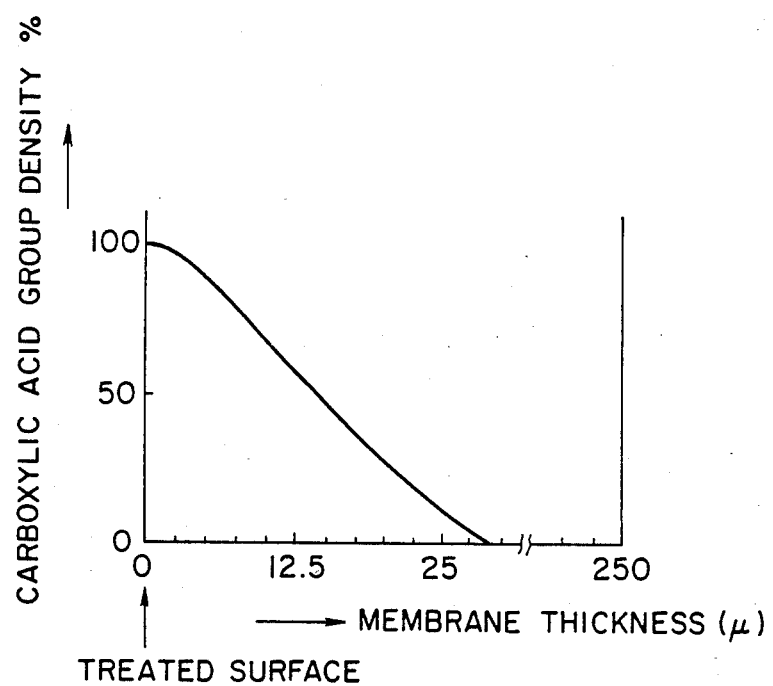

FLUORINATED ETHER ACYL FLUORIDES HAVING ALKYLTHIO OR ALKYLSULFONE GROUPS

This application is a divisional of copending application Ser. No. 299,164, filed on Sept. 3, 1981, now U.S. Pat. No. 4,510,328, which is, in turn, a divisional of application Ser. No. 152,847 filed on May 23, 1980, now U.S. Pat. No. 4,329,434.

This invention relates to a novel fluorinated cation exchange membrane having both carboxylic acid groups and sulfonic acid groups, intermediates and starting materials for production thereof and also to processes for producing such materials. This invention also concerns a novel fluorinated cation exchange membrane having sulfonic acid groups with a high ion-exchange capacity and being provided with physically high strength.

The cation exchange membrane according to the present invention can be used in electrolysis of an aqueous alkali metal halide solution under more severe conditions than those conventionally used while maintaining excellent performance stably for a long time.

In the chlor-alkali industry, wherein caustic soda and chlorine are produced by electrolysis of sodium chloride, the ion-exchange membrane process has recently attracted great attention, because it is more advantageous in various aspects such as prevention of environmental pollution and economical saving of energy than the mercury process and the diaphragm process of the prior art and also because it can produce caustic soda having substantially the same quality as that produced by the mercury process.

The greatest factor which controls the economy of the ion-exchange membrane process is the characteristic of the cation exchange membrane employed. It is necessary for the cation exchange membrane to satisfy the requirements as set forth below.

(1) To have a high current efficiency and a low electric resistance. In order to have a high current efficiency, the membrane is required to have a sufficiently high ion-exchange capacity and low water content, thus giving a high concentration of fixed ions in the membrane. On the other hand, to the effect of lower electric resistance, a higher water content is rather more advantageous. Since the water content will vary depending on the types of ion-exchange groups, the ion-exchange capacity and the concentration of external liquids, it is necessary to select the optimum combination of these factors.

(2) To be resistant to chlorine and alkali at higher temperatures for a long time. A cation exchange membrane comprising a fluorinated polymer can be sufficiently resistant generally under the aforesaid atmosphere, but some membranes may be insufficient in chemical stability depending on the ion-exchange groups contained therein. Accordingly, it is important to select suitable ion-exchange groups.

(3) To be durable for a long time under various stresses working in highly concentrated alkali under the conditions of high temperature and high current density such as a stress of swelling and shrinking, a stress accompanied by vigorous migration of substances to effect peel-off of layers and a stress by vibration of the membrane accompanied with gas generation to cause bending cracks. Generally speaking, the physical strength of the membrane is different depending on the physical structure of the membrane, the polymeric composition, the ion-exchange capacity and the types of ion-exchange groups. Therefore, it is necessary to realize the optimum selection of these factors.

(4) To be easily produced and low in cost.

In the prior art, there have been proposed several fluorinated cation exchange membranes for use in electrolysis of an aqueous alkali metal halide solution. For example, there is known a fluorinated cation exchange membrane having pendant sulfonic acid groups prepared by hydrolysis of a copolymer comprising tetrafluoroethylene and perfluoro-3,6-dioxa-4-methyl-7-octene sulfonylfluoride.

Such a well-known fluorinated cation exchange membrane containing only sulfonic acid groups, however, is liable to permit permeation of hydroxyl ions migrated and diffused from the cathode compartment therethrough due to the high water content afforded by the sulfonic acid groups. For this reason, such a membrane is disadvantageously low in current efficiency. In particular, when electrolysis is conducted, for example, by recovering a highly concentrated caustic soda solution of 20% or higher, the current efficiency is extremely low to a great economical disadvantage as compared with electrolysis by the mercury process or the diaphragm process of the prior art.

For improvement of such a drawback of low current efficiency, the ion-exchange capacity of sulfonic acid groups may be lowered to, for example, 0.7 milliequivalent or lower per one gram of the H-form dry resin, whereby the water content in the membrane can be decreased to make the fixed ion concentration in the membrane higher than the membrane with higher ion-exchange capacity. As the result, the current efficiency at the time of electrolysis can slightly be prevented from being lowered. For example, when electrolysis of sodium chloride is performed while recovering caustic soda of 20% concentration, the current efficiency can be improved to about 80%. However, improvement of current efficiency by reduction in ion-exchange capacity of the membrane will cause a noticeable increase in the electric resistance of the membrane, whereby no economical electrolysis is possible. Moreover, at any higher value of the electric resistance of the membrane, it is very difficult to prepare a commercially applicable sulfonic acid type fluorinated cation exchange membrane improved in current efficiency to about 90%.

On the other hand, British Pat. No. 1,497,748 and Japanese published unexamined patent application No. 126398/1976 disclose fluorinated cation exchange membranes having carboxylic acid groups as ion-exchange groups. In these membranes, the fixed ion concentration can be made higher due to the lower water content of carboxylic acid groups and therefore the current efficiency can be improved to 90% or higher. Such membranes are also chemically stable under the conditions conventionally used.

When compared at the same level of the ion-exchange capacity, however, the membrane having carboxylic acid groups is higher in electric resistance than the membrane having sulfonic acid groups. Particularly, when used at a high current density, the power unit may be undesirably very high. Moreover, perhaps due to lower water content throughout the membrane, the membrane is prone to shrink when used for a long time in a highly concentrated alkali under severe conditions until it is hardened so as to be brittle, resulting in layer peel-off or crack formation, whereby current efficiency may disadvantageously be lowered.

For improvement of such drawbacks of the membrane having only carboxylic acid groups, there is also known a cation exchange membrane prepared by bonding films of a fluorinated polymer having carboxylic acid groups or groups convertible to carboxylic acid groups (hereinafter referred to as precursors) and a fluorinated polymer having sulfonic acid groups or precursors thereof or by molding a blend of said polymers into a film, followed by hydrolysis, as disclosed by Japanese published unexamined patent applications No. 36589/1977 and No. 132089/1978 and U.S. Pat. No. 4,176,215. However, these polymers are poorly compatible with each other and it is difficult to effect complete bonding or blending. When used under severe conditions, such a membrane is liable to suffer from peel-off or formation of cracks and thereby to cause troubles. The blended product is also entirely insufficient from the standpoint of complete utilization of higher current efficiency of carboxylic acid groups and lower electric resistance of sulfonic acid groups. It merely exhibits the intermediate characteristic of both properties.

The aforesaid Japanese published unexamined patent applications and another Japanese published unexamined patent application No. 23192/1977 also disclose a cation exchange membrane prepared by ternary copolymerization of a vinyl monomer having carboxylic acid groups or precursors thereof, a vinyl monomer having sulfonic acid groups or precursors thereof and a fluorinated olefin, followed by fabrication into a film and hydrolysis. Such a membrane also merely shows the intermediate characteristic.

On the other hand, there are disclosed cation exchange membranes prepared by forming carboxylic acid groups by chemical treatment on one surface of fluorinated cation exchange membranes having sulfonic acid groups, as disclosed by U.S. Pat. No. 4,151,053, Japanese published unexamined patent applications No. 104583/1978, No. 116287/1978 and No. 6887/1979. These membranes, due to the presence of carboxylic acid groups, will effectively inhibit migration and diffusion of hydroxyl ions to exhibit higher current efficiency. Also, since the carboxylic acid groups are present in the thin layer on the cathode side and sulfonic acid groups with higher water content in the residual part of the membrane, the electric resistance of the membrane is low. Thus, these membranes are very excellent from the standpoint of power consumption. However, all of these membranes, while they are stably used with good performance under conventional conditions for a commercially satisfactory term, will suffer under severe conditions of further increased high current density and high temperature from swelling like splotch or formation of water bubbles, peel-off of the carboxylic acid layer from the sulfonic acid layer or formation of cracks in the carboxylic acid layer, thereby causing a decrease in current efficiency, as shown in the Comparative examples.

It has not yet been clarified why such pehnomena are caused. Presumably, the polymeric structure of the fluorinated cation exchange membrane having sulfonic acid groups or derivatives thereof may be one of the factors for such phenomena. That is, these membranes are prepared by chemical treatment of a copolymer of a fluorinated olefin with a sulfur containing fluorinated vinylether as represented by the following formula formed in the shape of a membrane or a hydrolyzed product thereof having sulfonic acid groups:

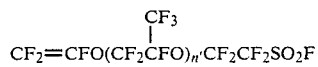

wherein n' is an integer of 0 to 2.

Among said monomers, the monomer of n'=0 will cause the cyclization reaction as shown by the reaction scheme (1) below in the vinylization step as disclosed by Japanese published examined patent application No. 2083/1972.

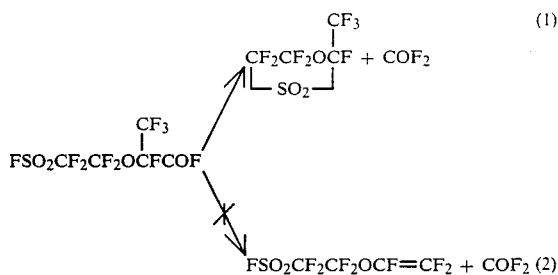

For converting the cyclic sulfone to $CF_2=CFOCF_2CF_2SO_2F$, a number of reaction steps are required to be performed and therefore it is very difficult to produce said monomer in commercial application. Moreover, depending on the conditions, such cyclization will also occur at the time of polymerization and may lower the properties of the resultant polymer.

For this reason, in commercial application, the monomer of n'=1 is conventionally used. With such a monomer, there is the drawback that the ion-exchange capacity of the resultant sulfonic acid type membrane and the membrane having formed carboxylic acid groups by chemical treatment on the surface of the sulfonic acid type membrane can limitedly be increased, as disclosed by the aforesaid Japanese published unexamined patent applications. Furthermore, perhaps due to the presence of the pendant groups:

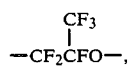

no physically tough membrane can be obtained unless the copolymerization ratio of a fluorinated olefin to the sulfur containing fluorinated vinyl ether is increased to about 6 or more. It is also expected that use of such a monomer may be one of the factors causing peel-off or cracks of the carboxylic acid layer formed when using the membrane having carboxylic acid groups and sulfonic acid groups as mentioned above under more severe conditions than conventionally used. The above drawbacks are further multiplied when the monomer of n'=2 having a larger molecular weight is used.

A copolymer of a fluorinated vinyl monomer having no ether linkage such as trifluorovinyl sulfonyl fluoride with tetrafluoroethylene, as disclosed by U.S. Pat. No. 3,624,053, is deficient in fabricability into a membrane.

Japanese published unexamined patent applications No. 28588/1977, No. 23192/1977 and No. 36589/1977 disclose fluorinated cation exchange membranes prepared from copolymers of fluorinated olefins with fluorinated vinyl compounds represented by the formula:

$$CF_2=CX^1(OCF_2CFX^2)_aO_b(CFX^3)_cSO_2X^4$$

wherein $X^1$ is F or $CF_3$, $X^2$ and $X^3$ are F or $C_1$-$C_{10}$ perfluoroalkyl, $X^4$ is F, OH, $OQ^1$, OM and $NQ^2Q^3$ ($Q^1$ is $C_1$-$C_{10}$ alkyl, $Q^2$ and $Q^3$ are H or one of $Q^1$, and M is an alkali metal or quaternary ammonium), a is an integer of 0 to 3, b an integer of 0 or 1 and c an integer of 0 to 12. However, these prior publications refer to no typical example of a process for preparation of said fluorinated vinyl compounds. Nothing is taught about precursors of said compounds. Moreover, as clearly seen from the description in the specifications of said Japanese published unexamined patent applications, there is only disclosure of the compounds, copolymers and membranes derived therefrom in the Examples and preferred typical examples which are those conventionally known of the formula:

$$CF_2=CFO(CF_2\overset{\overset{\displaystyle CF_3}{|}}{C}FO)_aCF_2CF_2SO_2F$$

wherein a is the same as defined above, namely the group of compounds wherein c is 2, although preferred embodiments are mentioned to be those wherein $X^1=F$, $X^2=CF_3$, $X^3=F$ or $CF_3$, $X^4=F$, $a=0$ to 1, $b=1$ and $c=1$ to 3.

In the field of ion-exchange membranes, it is strongly desired to develop a membrane which exhibits high current efficiency and low electric resistance under more severe conditions, has a longer life and can be produced at low cost. The present inventors have made efforts to develop such a membrane and consequently found that the above object can be attained by use of a novel fluorinated vinyl ether compound which is derived from starting materials having specific structure. The present invention has been accomplished based on such a finding.

The first object of the present invention is to provide a fluorinated carboxylic acid or its derivative represented by the formula:

$$X(CF_2)_nY$$

wherein X stands for $-SR^1$ or $-SO_2R^2$ ($R^1$ is an alkyl having 1 to 10 carbon atoms, an aryl, a perfluoroalkyl having 1 to 10 carbon atoms or chlorine; and $R^2$ is $R^1$ or $-OM$, M indicating hydrogen, a metal or ammonium group); Y stands for $-COY^1$ or $-CN$, y' being halogen, hydrogen, $-NH_2$, $-OM$ (M is the same as defined above), or $-OR^3$ ($R^3$ is an alkyl having 1 to 10 carbon atoms or an aryl); and n stands for an integer of 2 to 4, and a process for producing the same.

In the prior art, as a fluorinated compound having in combination carboxylic acid derivative groups and sulfonic acid groups or groups convertible thereto in the same molecule such as said fluorinated carboxylic acid derivative groups, there is known only the compound $FSO_2CF_2COF$ or the compound $$FSO_2\overset{\overset{\displaystyle CF_3}{|}}{C}FCFO,$$

as disclosed by U.S. Pat. No. 3,301,893. There is no suggestion about a compound comprising a fluorinated alkylene group having 2 to 4 carbon atoms $-CF_2-_n$ between the carboxylic acid derivative groups and sulfonic acid groups or the groups convertible thereto such as the compound according to the present invention.

The fluorinated carboxylic acid derivative according to the present invention can be prepared by converting the compound obtained by a process comprising the following step (A), (B) or (C) according to the reaction scheme (3), (4), (5) or (6), optionally in combination with various reactions such as acid treatment, hydrolysis treatment or halogenation treatment, into a carboxylic acid derivative and sulfonic acid derivative:

(A) A method comprising the step to react tetrafluoroethylene with a carbonic acid ester having 3 to 20 carbon atoms in the presence of a mercaptide represented by the formula $R'SM^1$ ($R'$ is an alkyl having 1 to 10 carbon atoms, an aryl or a perfluoroalkyl having 1 to 10 carbon atoms; $M^1$ is an alkali metal, ammonium group or a primary to quaternary alkylammonium group):

$$(3) \quad R'SM^1 + CF_2=CF_2 + \begin{matrix}R^4O\\ \phantom{x}\\ R^5O\end{matrix}\!\!\!\!>\!\!C=O \longrightarrow$$

$$R'SCF_2CF_2\overset{\overset{\displaystyle O}{\|}}{C}OR^4$$

or $$R'SCF_2CF_2\overset{\overset{\displaystyle O}{\|}}{C}CF_2CF_2SR'$$

(wherein $R^4$ and $R^5$ represent alkyl or aryl, and $M^1$ is the same as defined above);

(B) A method comprising the step to react tetrafluoroethylene with a compound of the formula: $A'_2SO_2$ ($A'$ is a halogen or an alkoxy having 1 to 5 carbon atoms) in the presence of an alkali cyanide:

$$NaCN + CF_2=CF_2 + A'_2SO_2 \rightarrow NCCF_2CF_2SO_2A' \qquad (4)$$

(wherein $A'$ is the same as defined above);

(C) A method comprising the step to react tetrafluoroethylene with a compound of the formula: $Z'SO_2F$ or $Z'_3CSO_2F$ ($Z'$ is a halogen except for F) in the presence of a free radical initiator:

$$(5) \quad Z'SO_2F + CF_2=CF_2 \xrightarrow{\text{free radical initiator}} Z'(CF_2)_4SO_2F$$

$$(6) \quad Z'_3CSO_2F + CF_2=CF_2 \xrightarrow{\text{free radical initiator}} Z'_3C(CF_2)_2SO_2F$$

or $$Z'_3C(CF_2)_4SO_2F$$

In the fluorinated carboxylic acid derivative of the present invention $X(CF_2)_nY$ (X, Y and n are the same as defined above), n may preferably be 2 when considering ease of preparation and the molecular weight of the fluorinated vinyl monomer prepared from said derivative. The group X may preferably be $-SR^1$ or $-SO_2R^1$, especially $X=-SR^1$ being preferred. As the group $R^1$, an alkyl having 1 to 10 carbon atoms or an aryl, especially an alkyl having 1 to 10 carbon atoms is preferred. Among them, an alkyl having 1 to 5 carbon atoms is most preferred. A compound wherein Y is $-COF$ is also desirable from the standpoint of usefulness as a starting material for the synthesis of a fluorinated vinyl compound. When Y is another carboxylic acid derivative, such a compound may be converted to a compound having the group Y=—COF.

Each of the methods (A), (B) and (C) is hereinafter described in further detail.

I. Method (A)

Examples of mercaptide to be used in the method (A) are derivatives of methyl mercaptan, ethyl mercaptan, propyl mercaptan, butyl mercaptan, amyl mercaptan, hexyl mercaptan, phenyl mercaptan, benzyl mercaptan, toluyl mercaptan, perfluoromethyl mercaptan, perfluoroethyl mercaptan, perfluoropropyl mercaptan, etc. in the form of sodium salts, potassium salts, cesium salts, ammonium salts, and primary to quaternary alkylammonium salts, preferably an alkyl mercaptan, especially having 1 to 5 carbon atoms, namely methyl-, ethyl-, propyl-, butyl- and amyl-mercaptan in the form of sodium salts or potassium salts.

The carbonic acid ester may be exemplified by dimethyl-, diethyl-, dipropyl-, dibutyl-, diphenyl-, or methylethyl-carbonate. Preferably, dimethyl carbonate and diethyl carbonate may be used.

The mercaptide and the carbonic acid ester are usually mixed in an inert medium. But no inert medium is necessarily required when said ester is liquid under the reaction conditions. Typical examples of a suitable inert medium are diethyl ether, tetrahydrofuran, dioxane, ethylene glycol dimethyl ether, diethylene glycol dimethyl ether, benzene and cyclohexane, having no active hydrogen and being capable of dissolving the carbonic acid ester.

The carbonic acid ester is used in an amount of 0.1 to 10 equivalents, preferably 0.5 to 5 equivalents, of the mercaptide.

Tetrafluoroethylene is usually employed in the gaseous state and may be fed into the reaction system under any desired pressure, irrespective of whether it may be pressurized, normal or reduced. Tetrafluoroethylene may be added in an amount of 0.1 to 5 equivalents, preferably 0.4 to 3 equivalents of the mercaptide.

The reaction is carried out usually at not higher than 100° C., preferably in the range from 80° to 0° C., until the pressure of tetrafluoroethylene is substantially constant under the reaction conditions employed. Formation of ketone leads to substantial decrease in the reaction yield based on the mercaptide. For this reason, it is preferred to use a lower temperature in order to suppress formation of the ketone in the reaction scheme (3). The reaction is carried out under substantially anhydrous conditions.

After completion of the reaction, the reaction system is made acidic by adding an acid. In this case, such a mineral acid as hydrochloric acid, sulfuric acid or phosphoric acid is usually used, sulfuric acid being preferred. The amount of mineral acid should be at least equivalent to the mercaptide initially employed.

In the above reaction procedure, there may also be used in place of the carbonic acid ester a N,N-dialkyl formamide having 3 to 7 carbon atoms, whereby a fluorinated aldehyde is obtained. Alternatively, in some cases, there may also be employed carbonic acid gas in place of the carbonic acid ester.

Isolation of ester, ketone or aldehyde which is the fluorinated carboxylic acid derivative may be performed by a conventional technique of separation such as phase separation, distillation or others. Said fluorinated carboxylic acid derivative of ester, ketone or aldehyde may be converted to various carboxylic acid derivatives according to suitable organic reaction procedures. For example, ester and ketone may be hydrolyzed with an alkali to give a carboxylic acid salt, which carboxylic acid salt may in turn be treated with a mineral acid to give a carboxylic acid. Further, the above carboxylic acid or salt thereof may be reacted with a chlorinating agent such as phosphorus pentachloride, thionyl chloride, etc. to obtain an acid chloride, or alternatively with sulfur tetrafluoride to obtain an acid fluoride. Also, according to the well known reaction to treat an acid chloride with sodium fluoride or potassium fluoride, an acid fluoride can be prepared. An acid fluoride is most useful from the standpoint of the starting material for synthesis of a fluorinated vinyl compound according to the reaction scheme (7) as shown below;

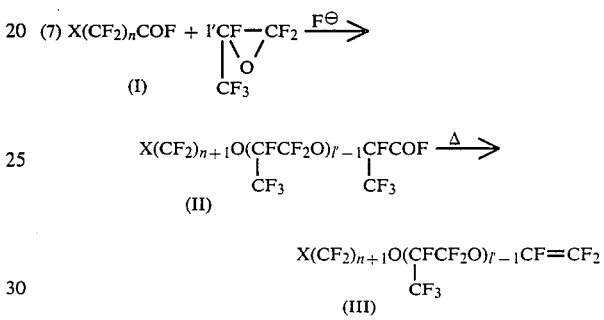

wherein n and X are the same as defined above, and l' is 1 or 2.

In the above fluorinated carboxylic acid derivative, the sulfide group present on the terminal end opposite to that of the carboxylic acid derivative group may also be converted to various derivatives according to suitable organic reaction procedures. For example, it may be converted by treatment with chlorine to the sulphenyl chloride group or sulfonyl chloride group, or by oxidation treatment to the sulfone group. Further, these groups may be subjected to hydrolysis treatment with an alkali to be converted to sulfonic acid group salts, which may be treated with phosphorus pentachloride to be converted to sulfonyl chloride groups. Conversion to such various derivative groups does not interfere with the reaction according to the scheme (7), insofar as such groups have no active hydrogen.

II. Method (B)

The alkali metal cyanide to be used in the method (B) may include cyanides of lithium, sodium, potassium, cesium, etc. Among them, cyanides of sodium and potassium may preferably be used.

Examples of the compound of the formula $A'_2SO_2$ are sulfuryl fluoride, sulfuryl chloride, sulfuryl bromide, sulfuryl chlorofluoride, sulfuryl bromofluoride, dimethyl sulfate, diethyl sulfate, dibutyl sulfate, diamyl sulfate, and the like. In some cases, there may also be used sulfur dioxide.

The alkali metal cyanide is used usually as a dispersion in an inert medium. When the compound $A'_2SO_2$ (A' is the same as defined above) is a liquid under the reaction conditions, no such inert medium is necessarily required to be used.

As a suitable inert medium, there may be mentioned solvents having no active hydrogen such as diethyl ether, tetrahydrofuran, dioxane, ethylene glycol dimethyl ether, diethylene glycol dimethyl ether, benzene, cyclohexane, etc. Said inert medium may desirably be capable of dissolving $A'_2SO_2$.

The $A'_2SO_2$ is used in an amount of 0.1 to 10 equivalents, preferably 0.5 to 5 equivalents of the alkali metal cyanide.

Depending on the $A'_2SO_2$ employed and the properties thereof, $A'_2SO_2$ is previously charged in the reaction system to be mixed with the alkali metal cyanide, or fed into the reaction system simultaneously with tetrafluoroethylene, or fed into the reaction system previously mixed with tetrafluoroethylene.

Tetrafluoroethylene is used usually under the gaseous state and may be fed into the reaction system under any desired pressure, whether it may be pressurized, reduced or normal.

Tetrafluoroethylene is added in an amount of 0.1 to 5 equivalents, preferably 0.4 to 3 equivalents of the alkali metal cyanide.

The reaction is carried out at not higher than 250° C., preferably at not higher than 100° C., until the pressure of tetrafluoroethylene is substantially constant under the reaction conditions employed. The reaction is conducted under substantially anhydrous conditions.

Separation of fluorinated nitrile may be performed according to such procedures as phase separation or distillation. Similarly as described in the method (A), said fluorinated nitrile may be converted to various carboxylic acid derivatives or sulfonic acid derivatives according to suitable organic reaction procedures, whereby it is most preferred that Y should be —COF.

III. Method (C)

The compound represented by the formula $Z'SO_2F$ or $Z'_3CSO_2F$ ($Z'$ is the same as defined above) to be used in the method (C) may be exemplified by sulfuryl chlorofluoride, sulfuryl bromofluoride, trichloromethane sulfonylfluoride, tribromomethane sulfonylfluoride, and the like. Among them, sulfuryl chlorofluoride and trichloromethane sulfonylfluoride are preferred.

As the free radical initiator, there may be employed most of those conventionally used in the field of organic chemical reactions. For example, it is possible to use organic peroxides such as benzoyl peroxide, di-t-butyl peroxide, perfluoroacetyl peroxide, di-t-amyl peroxide, etc. and azo-bis type compounds such as azobisisobutyronitrile, azobisisovaleronitrile, azobisnitrile, etc.

In the present invention, instead of permitting the free radical initiator to be present in the reaction, ultra-violet irradiation may be employed. Alternatively, it is also possible to effect irradiation of ultra-violet rays in the presence of a free-radical initiator.

Use of a solvent is not particularly limited, but there may be employed any solvent which is stable chemically to the free radical initiator or ultra-violet rays. Particularly, 1,1,2-trichloro-1,2,2-trifluoroethane and cyclohexane may preferably be used.

Tetrafluoroethylene is used in at least stoichiometric amount relative to $Z'SO_2F$ or $Z'_3CSO_2F$.

The amount of the free radical initiator used is in the range from 0.001% to 10% based on $Z'SO_2F$ or $Z'_3CSO_2F$.

The reaction temperature may suitably be determined in view of the half-life period of the free radical initiator or other factors, usually ranging from $-10°$ C. to 250° C., preferably from 0° C. to 150° C.

After completion of the reaction, the intermediates formed according to the reaction scheme (5) or (6) are isolated by phase separation or distillation from the reaction mixture, if desired. Said intermediates may be subjected to acid treatment using a mineral acid such as conc. sulfuric acid, sulfuric anhydride or fuming nitric acid to be converted to $HOOC(CF_2)_3SO_2F$ or $HOOC(CF_2)_4SO_2F$.

The above carboxylic acid may be isolated from the reaction mixture by isolation procedure such as extraction, phase separation or distillation. Similarly as described in the method (A), said carboxylic acid may be converted to various carboxylic acid derivatives according to suitable organic chemical reaction procedures. It is particularly preferred that Y should be —COF. Among various sulfonic acid derivatives, sulfonylfluoride groups can be converted to sulfone and sulfide groups.

According to another preparation method, it is also possible to carry out reaction between a disulfide and tetrafluoroethylene in the presence of a free radical initiator to give an intermediate having sulfide groups at both terminal ends of the molecule, which intermediate is then subjected to chlorine treatment to provide a compound having a sulfide group at one terminal end and a sulfonyl group at the other terminal end. By treatment of said compound with hydroiodic acid, there may also be prepared a compound having the sulfide group and the carboxylic acid group according to the present invention.

Alternatively, a compound having a sulphenylchloride group and sulphenyliodide group may be allowed to react with tetrafluoroethylene in the presence of a free radical initiator, followed by treatment of the resultant intermediate with an acid such as conc. sulfuric acid, sulfuric anhydride or fuming nitric acid, to provide the compound of the present invention having both a sulfide group and carboxylic acid group.

The compound of the present invention, especially an acid fluoride, is very useful for synthesis of a fluorinated vinyl ether compound having terminal groups convertible to sulfonic acid groups as shown in the reaction scheme (7). The above compound is also useful as starting materials for production of various materials such as surfactants, fiber treatment agents, lubricants, agricultural chemicals, etc.

The fluorinated carboxylic acid derivative of the present invention can also very advantageously be produced, since no such dangerous reaction is used such as the addition reaction between tetrafluoroethylene and $SO_3$ which will occur in the production of $FSO_2CF_2COF$ and also no toxic compound such as a cyclic sultone intermediate is involved.

The second object of the present invention is to provide a novel fluorinated acid fluoride represented by the formula:

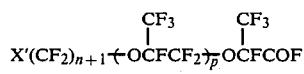

wherein $X'$ is —SR or $SO_2R$ (R is $C_1$–$C_{10}$ alkyl, $C_1$–$C_{10}$ perfluoroalkyl, aryl or chlorine), n is an integer of 2 to 4, p is an integer of 0 to 50, and a process for producing said fluorinated acid fluoride compound which comprises reacting a novel compound represented by the formula:

X'(CF$_2$)$_n$COF wherein X' and n are the same as defined above, with hexafluoropropyleneoxide, in the presence of a fluoride ion.

As a fluorinated compound having in combination an acid fluoride group and a functional group convertible to a sulfonic acid group in the same molecule such as said fluorinated acid fluoride compound, there is known in the prior art only a fluorinated acid fluoride of the following formula:

$$FSO_2(CF_2)_{l''}{+}OCFCF_2{\rightarrow}_{q'}OCFCOF$$
$$\quad\quad\quad\quad\quad\quad\quad |\quad\quad\quad\quad |$$
$$\quad\quad\quad\quad\quad\quad\quad CF_3\quad\quad\quad CF_3$$

wherein l''=2, q'=0-50, as disclosed by Japanese published examined patent application No. 1664/1967. No such compound of the present invention wherein l'' is 3 to 5 is suggested at all in the prior art.

The fluorinated acid fluoride of the present invention can be produced according to the following reaction scheme:

X'(CF$_2$)$_n$COF + (p + 1)CF$_3$CFCF$_2$ $\longrightarrow$
$\quad\quad\quad\quad\quad\quad\quad\quad\quad\quad\quad\;\,\backslash\,\,/$
$\quad\quad\quad\quad\quad\quad\quad\quad\quad\quad\quad\;\,\,O$ $$X'(CF_2)_{n+1}(OCFCF_2)_pOCFCOF$$
$$\quad\quad\quad\quad\quad\quad\;\, |\quad\quad\quad\quad |$$
$$\quad\quad\quad\quad\quad\quad\;\, CF_3\quad\quad\quad CF_3$$

wherein X', n and p are the same as defined above.

The reaction between the compound of the formula X'(CF$_2$)$_n$COF (wherein X' and n are the same as defined above) and hexapropylene oxide may preferably be conducted in the presence of a fluoride ion as catalyst. This can easily be done by use of a suitable fluoride, including alkali metal fluorides such as cesium fluoride, potassium fluoride, etc.; silver fluoride; ammonium fluoride; C$_1$-C$_4$ tetraalkyl ammonium fluoride such as tetramethyl ammonium fluoride, tetraethyl ammonium fluoride and tetrabutyl ammonium fluoride; and so on.

The fluoride catalyst is usually used together with an inert liquid diluent, preferably an organic liquid, which can dissolve at least 0.001% of the fluoride selected. The fluoride catalyst may be used in an amount of about 0.01 to about 2 mole equivalent per one mole of the compound represented by the formula X'(CF$_2$)$_n$COF wherein X' and n are the same as defined above. Examples of suitable diluents are polyethers such as ethyleneglycol dimethylether, diethyleneglycol dimethylether, tetraethyleneglycol dimethylether, etc. and nitriles such as acetonitrile, propionitrile, etc. The reaction is slightly exothermic and therefore there should be provided a means for dissipating the reaction heat.

The reaction temperature may be in the range from about −50° C. to about 200° C., preferably from about −20° C. to about 150° C. The pressure is not a critical parameter and may either be lower than or not lower than the atmospheric pressure. The reaction time may usually be from 10 minutes to 100 hours. The applicable molar ratio of hexapropylene oxide to X'(CF$_2$)$_n$COF is from about 1/20 to about 100/1. When the compound $$X'(CF_2)_{n+1}(OCFCF_2)_pOCFCOF$$
$$\quad\quad\quad\quad\quad\quad\;\, |\quad\quad\quad\quad |$$
$$\quad\quad\quad\quad\quad\quad\;\, CF_3\quad\quad\quad CF_3$$

has a low p value, for example, when p is 0 or 1, the relative proportion of X'(CF$_2$)$_n$COF is increased, and lower pressure and higher temperature are preferred to be selected. On the other hand, when a product with a high p value is desired to be prepared, it is preferred to increase the relative proportion of hexapropylene oxide and select higher pressure and lower temperature.

In the fluorinated acid fluoride of the present invention, $$X'(CF_2)_{n+1}(OCFCF_2)_pOCFCOF$$
$$\quad\quad\quad\quad\quad\quad\;\, |\quad\quad\quad\quad |$$
$$\quad\quad\quad\quad\quad\quad\;\, CF_3\quad\quad\quad CF_3$$

wherein X', n and p are the same as defined above, a compound wherein n=2 and also a compound wherein X'=—SR are preferred from the standpoint of ease of preparation. As the group R, C$_1$-C$_{10}$ alkyl or an aryl, especially C$_1$-C$_{10}$ alkyl is preferred. Among them, C$_1$-C$_5$ alkyl is most preferred.

On the other hand, a cation exchange membrane prepared from a copolymer of said fluorinated vinyl ether compound and tetrafluoroethylene may desirably have an ion-exchange capacity as large as possible. From this standpoint, said fluorinated vinyl ether compound may preferably have a molecular weight as small as possible. Accordingly, it is preferred that the value of p may be 0 or 1, most preferably 0.

The compound represented by the formula:

$$X'(CF_2)_{n+1}(OCFCF_2)_pOCFCOF$$
$$\quad\quad\quad\quad\quad\quad\;\, |\quad\quad\quad\quad |$$
$$\quad\quad\quad\quad\quad\quad\;\, CF_3\quad\quad\quad CF_3$$

wherein X', n and p are the same as defined above is useful as an intermediate for the preparation of a novel fluorinated vinylether compound having functional groups convertible to sulfonic acid groups. Said compound is also useful as a starting material for surfactants, fiber treatment agents, lubricants, agricultural chemicals, etc.

The third object of the present invention is to provide a novel fluorinated vinylether compound represented by the formula:

$$X'(CF_2)_{n+1}{+}OCFCF_2{\rightarrow}_{p'}OCF{=}CF_2$$
$$\quad\quad\quad\quad\quad\quad\;\, |$$
$$\quad\quad\quad\quad\quad\quad\;\, CF_3$$

wherein X' is —SR or SO$_2$R (R is C$_1$-C$_{10}$ alkyl, an aryl, C$_1$-C$_{10}$ perfluoroalkyl or chlorine, n an integer of 2 to 4 and p' an integer of 0 to 5, and a process for preparing the same.

As a fluorinated vinylether compound having functional groups convertible to sulfonic acid groups such as said fluorinated vinylether compound, there is known in the prior art only the class of compounds:

$$FSO_2(CF_2)_{l''}{+}OCFCF_2{\rightarrow}_{m'}OCF{=}CF_2$$
$$\quad\quad\quad\quad\quad\quad\quad |$$
$$\quad\quad\quad\quad\quad\quad\quad CF_3$$

wherein $l''=2$ and $m'=0$ to 2. Nothing is suggested in the prior art about the compounds of the present invention wherein $l''$ is 3 to 5.

The fluorinated vinylether compound of the present invention can be prepared according to the following reaction schemes:

I 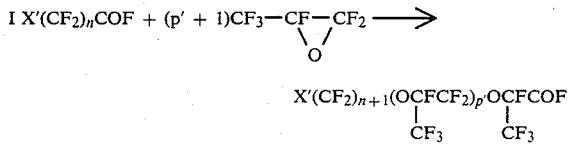

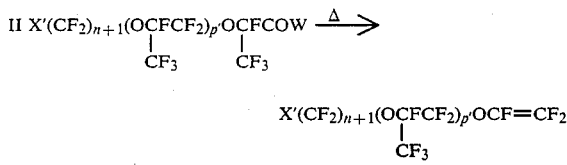

II $X'(CF_2)_{n+1}(OCFCF_2)_{p'}OCFCOW \xrightarrow{\Delta}$
           |      |
          CF$_3$   CF$_3$

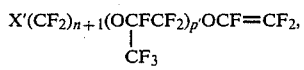

wherein $X'$, n and $p'$ are the same as defined above and W is F or OM' (M' is an alkali metal).

The fluorinated vinylether compound of the present invention represented by the formula

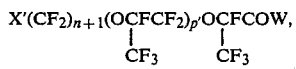

wherein $X'$, n and $p'$ are the same as defined above, can be prepared by pyrolysis of the compound of the formula:

$X'(CF_2)_{n+1}(OCFCF_2)_{p'}OCFCOW,$
          |      |
         CF$_3$   CF$_3$ wherein $X'$, n, $p'$ and W are the same as defined above, according to the aforesaid scheme (II). In said reaction, it is preferred to use a compound wherein $W=F$ from the standpoint of ease of use in the reaction.

Said reaction can be practiced under substantially anhydrous conditions under either pressurized, normal or reduced pressure. Usually, however, the reaction may conveniently be practiced under normal or reduced pressure.

There may also be employed a diluent to a dilution degree of 0 to 100 depending on the mode of reaction, said diluent being selected from inert gases such as nitrogen, helium, carbon dioxide, argon, etc. or inert non-protonic liquids such as polyethers.

When the terminal group is an acid fluoride group, it is possible and desirable to carry out the reaction in the presence of a metallic salt or a metal oxide. In this case, there may preferably be used a solid base which can decompose any corrosive and toxic $COF_2$ generated such as sodium carbonate, potassium carbonate, sodium phosphate, potassium phosphate, etc.

The reaction temperature may range from 100° to 600° C., preferably from 100° to 350° C. If the temperature is too high, side reactions such as decomposition other than vinylization are liable to occur. At too low a temperature, conversion of the starting material is lowered. The reaction time may be from 0.1 second to 10 hours, preferably from 10 seconds to 3 hours. The reaction temperature and the reaction time should suitably be selected to provide optimum conditions, for example, shorter reaction time at higher reaction temperature or longer reaction time at lower reaction temperature.

In the prior art, it has been deemed commercially difficult to prepare $FSO_2(CF_2)_2OCF=CF_2$ by a process comprising pyrolyzing

(m' is the same as defined above) to form the corresponding fluorinated vinylether compound

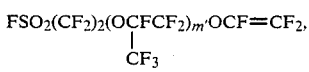

because a cyclization reaction will occur when m' is 0.

In contrast, according to the present invention, use is made of the fluorinated acid fluoride represented by the formula

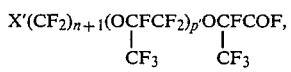

wherein $X'$, n and $p'$ are the same as defined above. Thus, due to the difference in size of the ring, pyrolysis can be effected while causing no or only a negligible cyclization reaction. Therefore, it is possible to produce easily a fluorinated vinylether compound represented by the formula:

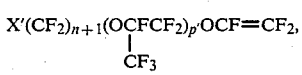

wherein $X'$, n, $p'$ are the same as defined above, even when $p'$ may be 0. Said fluorinated vinylether compound is also free from cyclization during polymerization, thereby causing no deterioration of properties of the resultant polymer.

In the fluorinated vinylether compound of the present invention

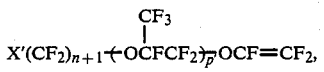

wherein $X'$, n and $p'$ are the same as defined above, it is preferred from the standpoint of ease of preparation that n is equal to 2 and $X'$ equal to $-SR$. In said group, R may preferably be $C_1-C_{10}$ alkyl or an aryl, especially $C_1-C_{10}$ alkyl, most preferably $C_1-C_5$ alkyl.

On the other hand, the cation exchange membrane to be prepared from the copolymer of said fluorinated vinylether compound and tetrafluoroethylene is desired to have an ion-exchange capacity as large as possible. From this standpoint, said fluorinated vinylether compound may preferably be one wherein $p'$ is equal to 0 or 1, especially $p'=0$ being preferred.

The fluorinated vinylether compound of the present invention can be copolymerized with, for example, tetrafluoroethylene to give a fluorinated cation exchange membrane which has the very excellent characteristic of sufficiently high ion-exchange capacity while maintaining good mechanical strength.

The fluorinated vinylether compound of the present invention may also be useful as an intermediate for synthesis of various fluorinated compounds having functional groups containing a sulfur atom at the terminal end of the molecule, for example, surfactants, fiber treating agents, lubricants, etc. It is also possible to prepare a fluorinated elastomer comprising a copolymer of the above fluorinated vinylether compound with a fluorinated olefin using said compound as a constituent or crosslinking monomer of said elastomer.

The fourth object of the present invention is to provide a novel fluorinated copolymer comprising the following recurring units (A) and (B):

$$-(CA_1A_2-CA_3A_4)- \quad (A)$$

($A_1$ and $A_2$ are F or H; $A_3$ is F, Cl or H; $A_4$ is F, Cl, $CF_3$, $-OR_F$, H or $CH_3$, $R_F$ being $C_1$-$C_5$ perfluoroalkyl)

$$-(CF_2-CF)- \quad CF_3 \quad (B)$$
$$\quad | \qquad\qquad |$$
$$\quad O-(CF_2CFO)_k(CF_2)_l-Z-R$$

($k = 0$ or 1; $l$ is an integer of 3 to 5; Z is $-S-$ or $-SO_2-$; R is $C_1$-$C_{10}$ alkyl, an aryl, Cl or $C_1$-$C_{10}$ perfluoroalkyl)

and a process for producing the same. In the above copolymer, the ratio of the numbers of recurring unit (A)/(B) is desired to be in the range from 1 to 16.

When the copolymer is required particularly strongly to have resistance to heat and chemicals, as is required in preparation of a fluorinated cation exchange membrane for use in electrolysis of an aqueous alkali metal halide solution, the recurring unit (A) in the above formula may preferably be:

$$-(CF_2CF)-$$
$$\quad\quad |$$
$$\quad\quad L$$

(L is F, Cl, $CF_3$, $-OR_F$ or H, $R_F$ being the same as defined above). It is particularly preferred that L should be F.

In order to produce membranes or resins having high ion-exchange capacity and physical toughness, the notation k may preferably be zero. The ratio (A)/(B) is preferred to be in the range from 1.5 to 14, more preferably from 3 to 11.

From the standpoint of ease of preparation of the monomer, the physical properties of the resultant polymer and possible greater variety of the polymer properties, it is also preferred that $l$ should be equal to 3 and R should be $C_1$-$C_{10}$ alkyl or an aryl, $C_1$-$C_{10}$ alkyl being especially preferred. When taking also polymerizability and moldability into consideration, a monomer wherein Z is $-S-$ and R is $C_1$-$C_{10}$ alkyl, especially $C_1$-$C_5$ alkyl may preferably be used.

The above copolymer is substantially a random copolymer having a molecular weight generally in the range from 8,000 to 1,000,000, having a melt index generally in the range from 0.001 g/10 min. to 500 g/10 min., as measured by use of an orifice of 2.1 mm in diameter and 8 mm in length, under a load of 2.16 kg at 250° C.

The above copolymer may conveniently be identified by measurement of the infrared absorption spectrum (IR) or attenuated total reflection (ATR) of a film of the copolymer, as shown in the Examples.

The compositions of the copolymer is estimated by measurement of the ion-exchange capacity, elemental analysis or a combination thereof after converting all of the sulfur containing terminal groups to ion-exchange groups such as sulfonic acid groups or carboxylic acid groups.

The structure of the pendant groups contained in the copolymer according to the present invention can also be identified by the measurement of IR or ATR of the product formed by converting the sulfur containing terminal groups to ion-exchange groups such as sulfonic acid groups, carboxylic acid groups or sulfinic acid groups and then carrying out the reaction for elimination of said ion-exchange groups.

The fluorinated copolymer of the present invention can be prepared by copolymerization of at least one monomer selected from the group consisting of the olefins of the formula:

$$CA_1A_2=CA_3A_4$$

wherein $A_1$, $A_2$, $A_3$ and $A_4$ are the same as defined above, at least one monomer selected preferably from the group consisting of the fluorinated olefins of the formula:

$$CF_2=CFL$$

wherein L is F, Cl, $CF_3$, $-OR_F$ or H, $R_F$ being $C_1$-$C_5$ perfluoroalkyl, and at least one monomer selected from the group consisting of sulfur containing fluorinated vinylether compounds of the formula:

$$CF_3$$
$$|$$
$$CF_2=CFO(CF_2CFO)_k-(CF_2)_l-Z-R$$

wherein k, l, Z and R are the same as defined above.

In this case, there may also be copolymerized a minor amount of other vinyl compounds mixed with the above monomers. It is also possible to effect crosslinking by copolymerization of a divinyl compound such as perfluorobutadiene or perfluorodivinylether or a fluorinated vinyl compound having terminal groups capable of effecting a crosslinking reaction such as $CF_2I$, etc.

The fluorinated olefin to be used in the present invention may preferably be one containing no hydrogen atom from the standpoint of heat resistance and chemical resistance of the resultant copolymer. Above all, tetrafluoroethylene is most preferred.

Among the sulfur containing fluorinated vinylether compounds, those wherein $k=0$ are preferred for providing membranes with greater ion-exchange capacity and excellent physical toughness. Of course, there may also be used a minor amount of the compound wherein $k=1$. The class of compound wherein $l=3$ is also preferred from the standpoint of ease of preparation as well as the physical properties of the resultant polymer. A compound with $l=6$ or more can only be produced with difficulty and can provide no membrane having sufficiently high ion-exchange capacity, thus being inferior to those with $l=3$ to 5.

The group R may preferably be $C_1$-$C_{10}$ alkyl or an aryl in view of the ease in preparation of the vinyl monomer. Among them, $C_1$-$C_{10}$ alkyl group is more preferable.

When taking also polymerizability and moldability into consideration, it is especially preferred to use a compound wherein Z is $-S-$ and R is $C_1$-$C_{10}$ alkyl.

Typical examples of the sulfur containing fluorinated vinylether compounds preferably used in the present invention are as follows:

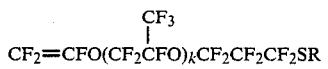

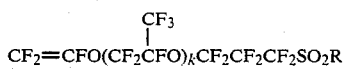

wherein k is 0 or 1, preferably 0, R is $C_1$–$C_{10}$ alkyl or an aryl.

As compared with the sulfur containing vinylether compound conventionally used in the prior art for preparation of fluorinated cation exchange membranes or fluorinated cation exchange resins having sulfonic acid groups and/or carboxylic acid groups, the sulfur containing fluorinated vinylether compound of the present invention is substantially free from or remarkably decreased in such cyclization reaction as previously described in the vinylization step, even when k=0, due to the difference in the number of members constituting the ring. Thus, a compound with k=0 can also easily be produced. Also during polymerization, there is no deterioration of the polymer properties due to a cyclization reaction. Accordingly, vinylether compounds with k=0 can principally be used in polymerization to provide a fluorinated copolymer containing substantially no or only a minor amount of pendant

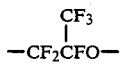

groups. As the result, the content of fluorinated olefin can be increased at the same level as the ion-exchange capacity of the membranes or resins, whereby there can be obtained membranes or resins having higher ion-exchange capacity and also having good physical toughness.

The ratio of the olefin and the sulfur containing fluorinated vinyl ether compound to be copolymerized can be controlled by suitable selection of the ratio of monomers charged and the polymerization conditions.

The copolymer of the present invention may be prepared according to well known polymerization methods used for homopolymerization or copolymerization of a fluorinated ethylene. The methods for preparation of the copolymer of the present invention may include both a method in which polymerization is conducted in a non-aqueous system and a method in which polymerization is conducted in an aqueous system. The polymerization temperature may generally range from 0° to 200° C., preferably from 20° to 100° C. The pressure may be from 0 to 200 kg/cm$^2$, preferably from 1 to 50 kg/cm$^2$. The non-aqueous polymerization may frequently be carried out in a fluorinated solvent. Suitable non-aqueous solvents may include inert 1,1,2-trichloro-1,2,2-trifluoroethane or perfluoro-hydrocarbons, e.g. perfluoromethylcyclohexane, perfluorodimethylcyclobutane, perfluorooctane, perfluorobenzene, etc.

As an aqueous polymerization method for preparation of the copolymer, there may be mentioned an emulsion polymerization method wherein monomers are brought into contact with an aqueous medium containing a free radical initiator and an emulsifier to provide a slurry of polymer particles or a suspension polymerization method wherein monomers are brought into contact with an aqueous medium containing both free radical initiator and dispersion stabilizer inert to telomerization to provide a dispersion of polymer particles, followed by precipitation of the dispersion. As the free radical initiator to be used in the present invention, there are redox catalysts such as ammonium persulfate-sodium hydrogen sulfite, etc.; organic peroxides such as t-butyl peroxide, benzoyl peroxide, etc.; azo-bis type compounds such as azobisisobutyronitrile, and fluorine radical initiators such as $N_2F_2$, etc.

After polymerization, the polymer may be molded into membranes or granules, if desired. a conventional technique may be used for molding the polymer into a thin film or pellets by melting the polymer.

The copolymer of the present invention is useful as a starting material for preparation of a fluorinated cation exchange membrane having sulfonic acid groups and/or carboxylic acid groups. In this case, the above membrane may, sometimes preferably, be laminated with a membrane made from a copolymer having a greater copolymerization ratio of the sulfur containing fluorinated vinylether compound. As the membrane to be laminated, there may be used a membrane prepared from the copolymer of the monomers selected from the group of the above sulfur containing fluorinated vinylether compounds and the groups of fluorinated olefins. Alternatively, there may also be employed a membrane prepared from the following sulfur containing fluorinated vinylether compound:

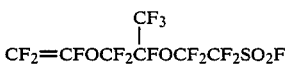

The membrane to be used for lamination may preferably have a thickness of ½ to 19/20 times the thickness of the entire laminated product in order to make the electric resistance thereof smaller.

The above membrane can be reinforced in strength by backing with a mechanical reinforcing material such as a net. As such backing materials, there may most suitably be used a net made of polytetrafluoroethylene fibers. A porous polytetrafluoroethylene sheet is also useful.

It is also possible to increase the strength of the membrane by incorporating polytetrafluoroethylene fibers during molding into a membrane. When a membrane with a laminated structure is employed, the reinforcing material may preferably be embedded on the side of the membrane with the greater copolymerization ratio of sulfur containing fluorinated vinylether compound. Reinforcing materials may be embedded in the membrane by a method such as laminating, press contact embedding or vacuum fusion embedding. For example, when a net is to be embedded, a membrane is placed on a net and the surface of the membrane opposite to that contacted with the net is heated to a temperature no higher by 20° C. than the melting point of the membrane and the surface of the membrane contacted with the net maintained at a temperature higher by at least 60° C. than the melting point of the membrane, while providing pressure a difference between both sides of the membrane. The pressure on the side contacted with the net is made lower than the opposite side.

Other than the above method, it is also possible to embed the net in the membrane after converting the exchange groups on the side opposite to that contacted with the net to carboxylic acid esters.

The thickness of the membrane is generally 2500 microns or less, preferably 1000 micron or less, more preferably 500 microns or less. The lower limit is restricted by the mechanical strength required, but usually 10 microns or more.

The copolymer of the present invention may be formed into particles during polymerization or molding according to conventional procedures for preparation of ion-exchange resins, and then subjected to the reaction used for converting a membrane into a fluorinated cation exchange membrane to provide fluorinated ion-exchange resin particles.

These ion-exchange resins can be processed into any desired shape such as granules, membranes, fibers, strands, etc. By utilization of heat resistance and chemical resistance superior to hydrocarbon type resins, they are useful generally in separation processes which are based on adsorption properties such as adsorptive separation of metallic ions or separation of organic high molecular substances. They are also useful as acid catalysts for organic reactions.

The copolymer according to the present invention can also be used in the form of fibers or strands as ion-conductive reinforcing material for a fluorinated cation exchange membrane.

Said copolymer may also be blended with other fluorocarbon type or hydrocarbon type copolymers to provide various blends useful for various purposes. It may also be provided as it is or as a mixture with a suitble solvent for use as lubricants, surfactants, etc. It is also useful as the starting material for a fluorinated elastomer.

The fifth object of the present invention is to provide a novel fluorinated cation exchange membrane for use in electrolysis of an aqueous alkali metal halide solution, comprising the following recurring units (C), (D) and (E):

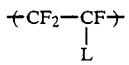   (C)

(L is F, Cl, CF$_3$, OR$_F$ or H, R$_F$ being C$_1$-C$_5$ perfluoroalkyl)

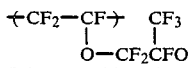   (D)

(k is 0 or 1, l is an integer of 3 to 5; M is H, metal or ammonium ion);

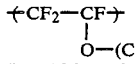   (E)

(k and M are the same as defined above and m is (l − 1)), and having a carboxylic acid group density, which is defined as the percentage of the number of carboxylic acid groups based on the total number of all ion-exchange groups present in a layer substantially parallel to the surfaces of the membrane, of at least 20% on one surface of the membrane, said carboxylic acid group density being gradually decreased toward the innerside of the membrane from said one surface of the membrane, and also a process for producing the same. In the above cation exchange membrane, the relative proportion of the recurring units (C)/[(D)+(E)] may preferably be in the range from 1.5 to 14. It is also preferred that the density of carboxylic acid groups across the membrane should be decreased moderately enough such that the gradient in terms of the decreased percentage of carboxylic acid groups per unit thickness may be 20%/micron at its maximum.

One specific feature of the membrane according to the present invention resides in having excellent electrolysis performance of high current efficiency and low electrolysis voltage. Another specific feature of the membrane resides in stability under more severe conditions than those usually employed, whereby said excellent electrolysis performance can be maintained for a long time. The membrane can also be produced economically with ease and at low cost.

The excellent electrolysis performance of the membrane according to the present invention may be ascribed to the specific structure of the membrane, having a carboxylic acid group density on one surface of 20% to 100%, preferably 40% or more, more preferably 60% or more, said carboxylic acid group density gradually decreasing from said one surface toward the innerside of the membrane, i.e. in the direction of thickness of the membrane. To give a quantitative expression of such a gradual decrease of carboxylic acid group density from one surface of the membrane toward the depth of the membrane in terms of the maximum gradient, which is defined as the greatest decrease of carboxylic acid group density per unit thickness in the membrane, the maximum gradient should preferably be 20 to 0.1% per one micron of the membrane thickness, more preferably 10% to 1%. As a preferable structure, said carboxylic acid group density may reach substantially zero % at a depth of not more than ½ of the entire thickness of the membrane from one surface. In other words, the carboxylic acid groups should preferably be present in the membrane locally in one half side of the membrane, being more enriched with a gradual increase the nearer to the surface on one side, while the other half side of the membrane contains other exchange groups, namely sulfonic acid groups. More preferably, the depth at which the carboxylic acid group density reaches zero % may be less than ½ of the entire thickness of the membrane, i.e. ¼ or less, most preferably 1/6 or less, to the lower limit of about 1μ.

When the membrane of the present invention is used for electrolysis of an aqueous alkali metal halide solution, it is preferred to use the membrane with the surface having higher carboxylic acid group density facing toward the cathode. With such an arrangement, said surface shrinks when contacted with a highly concentrated alkali due to the presence of carboxylic acid groups to increase the concentration of fixed ions. As the result, permeation, migration and diffusion of hydroxyl ions into the membrane can effectively be inhibited, whereby high current efficiency can be exhibited.

The carboxylic acid group density on said one surface of the membrane may be variable depending on various factors such as the value of the ratio (C)/[(D)+(E)], the current density, the temperature and the alkali concentration employed in electrolysis and can be optimally determined by controlling the conditions in preparation. Generally speaking, as the value of (C)/[(D)+(E)] is greater, the carboxylic acid group density may be lower.

On the other hand, according to a preferred embodiment of the membrane of the present invention, carboxylic acid groups are present primarily in a thin layer on the side of one surface of the membrane, only sulfonic acid groups being present in most of the residual portion. For this reason, the electric resistance in migration of alkali metal ions from the anode chamber to the cathode chamber is extremely low as compared with, for example, a membrane containing only carboxylic acid groups. Due to the presence of sulfonic acid groups, the water content in the membrane as a whole is also very large as compared with a membrane containing only carboxylic acid groups and therefore the membrane can be free from hardening or embrittlement due to shrinkage of the membrane even when used under severe conditions in a highly concentrated alkali for a long term.

One reason why the membrane of the present invention can be used more stably than the membrane of the prior art even under more severe conditions than those conventionally used may be ascribed to the specific structure of the polymer substantially consisting of the recurring units (C), (D) and (E) as described above. For obtaining a membrane having high ion-exchange capacity as well as good physical toughness, it is preferred that the suffix k should be equal to zero, but there may also be partially mixed therewith a polymer wherein k is one. It is also preferred from the ease of preparation of the monomer, the physical properties of the resultant polymer and greater variable range of the polymer properties that the suffix l should be equal to 3. A membrane with an l value of 6 or more is inferior to those with l values of 3 to 5 from the standpoint of difficulty in commercial production of the monomer and insufficient ion-exchange capacity obtained. A membrane wherein L is a fluorine atom is particularly preferred from the aspects of heat resistance and chemical resistance.

The specific feature of the polymer structure as mentioned above is based on the specific structure of the sulfur containing fluorinated vinylether of the following formula used for preparation of the membrane of the invention:

$$CF_2=CFO(CF_2CFO)_k-(CF_2)_l-Z-R$$
$$\phantom{CF_2=CFO(}|\phantom{CFO)_k-(CF_2)_l-Z-R}$$
$$\phantom{CF_2=CFO(CF_2}CF_3$$

wherein k and l are the same as defined above, Z is —S— or —SO$_2$—, R is C$_1$–C$_{10}$ alkyl, an aryl Cl or C$_1$–C$_{10}$ perfluoroalkyl.

The above monomer is different in the structure of the terminal end or in the number of members of the ring in the product by-produced in the vinylization step, as compared with the sulfur containing fluorinated vinylether of the formula:

$$CF_2=CFO+CF_2CFO)_{n'}CF_2CF_2SO_2F$$
$$\phantom{CF_2=CFO(}|$$
$$\phantom{CF_2=CFO(}CF_3$$

wherein n' is an integer of 0 to 2, which is used as starting material for a sulfonic acid type membrane of the prior art or a sulfonic acid type membrane having been formed by chemical treatment of carboxylic acid groups in the surface stratum thereof, and therefore it is possible to form substantially no or to decrease to a great extent the cyclization reaction in the vinylization step as mentioned above. Thus, a monomer with k=0 can easily be prepared and there is also no deterioration of polymer properties due to cyclization during polymerization.

Accordingly, since it is possible to use a monomer with k=0 as principal starting material for preparation of a membrane, the resultant polymer can have a structure containing substantially no only or a very small proportion of pendant groups:

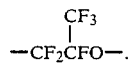

Consequently, with the same level of the ion-exchange capacity, the content of fluorinated olefin can be increased. In other words, there can be produced a physically tough membrane with enhanced ion-exchange capacity. Moreover, while its mechanism has not yet been clarified, such a membrane can maintain stable performance, being prevented from encountering problems of peel-off or crack of the carboxylic acid layer, even when used under more severe conditions than those conventionally used.

Another reason why the membrane of the present invention is stable under severe conditions may be ascribed to the relative ratio of the recurring units (C), (D) and (E), i.e. the ratio of (C)/[(D)+(E)] which is generally in the range from 1.5 to 14, preferably from 3 to 11, more preferably from 3.5 to 6. When said ratio is less than 1.5, the membrane is liable to be swelled during usage and therefore cannot maintain stable performance for a long term. On the other hand, if it is greater than 14, the membrane is liable to shrink so as to make the electric resistance of the membrane impractically high.

The ion-exchange capacity of the membrane according to the present invention may be represented by the following formulas as being dependent on the structure of the recurring units, the ratio of recurring units and the carboxylic acid group density:

| Ion-exchange capacity = | 1000/[r(81 + M$_L$) + d(142 + 166k + 50m) + (1 − d) (178 + 166k + 50l)] (meq/g-dry H-form resin) |
|---|---| wherein r=(C)/[(D)+(E)], M$_L$ is the molecular weight of the atomic group L and d is the carboxylic acid group density, k, l and m being the same as defined above.

In the prior art, the ion-exchange capacity of an ion-exchange capacity has been indicated in specific numerical values, as disclosed by Japanese published unexamined patent applications No. 120492/1975, No. 130495/1976, No. 36589/1977 and No. 24176/1977, and U.S. Pat. No. 4,065,366. According to the study by the present inventors, however, the swelling and shrinking behavior of a membrane with a given species of ion-exchange groups is not controlled by the ion-exchange capacity per se of the membrane but by the most important factors including the fluorinated olefin constituting the copolymer, the copolymer ratio of the fluorinated vinylether having ion-exchange groups and the presence or absence of

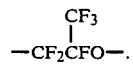

In order to obtain a membrane having sufficiently low electric resistance and good physical toughness with small swelling or shrinking when used in electrolysis, it is required to use a fluorinated vinylether having no $$-CF_2CFO-$$
$$\phantom{-CF_2C}|\phantom{O-}$$
$$\phantom{-CF_2CF}CF_3$$

groups as principal components and to control the above copolymerization ratio within a certain range. The ion-exchange capacity as represented by the above formula is based on such considerations.

It is not clear why the above copolymerization ratio has such a decisive influence on the swelling and shrinking behavior of a membrane. For convenience of explanation, reference is made to a membrane the containing most preferred fluorinated olefin, i.e. tetrafluoroethylene. From analysis of X-ray diffraction of the membrane, tetrafluoroethylene seems to be partially crystallized. Since the degree of crystallization is greatly dependent on the above copolymerization ratio, it may be estimated that the crystallized region will function as quasi-crosslinks which control the swelling and shrinking behavior of the membrane.

In the membrane according to the present invention, it is possible to provide a structure containing substantially no or a small amount of pendant groups:

$$-CF_2CFO-.$$
$$\phantom{-CF_2C}|\phantom{O-}$$
$$\phantom{-CF_2CF}CF_3$$

When a membrane with the same ion-exchange capacity is to be prepared, the copolymerization ratio of tetrafluoroethylene can be increased in the membrane of the present invention, as compared with a membrane prepared by use of $$CF_2=CFOCF_2CFOCF_2CF_2SO_2F$$
$$\phantom{CF_2=CFOCF_2C}|$$
$$\phantom{CF_2=CFOCF_2}CF_3$$

as a sulfur containing fluorinated vinylether, thereby providing a membrane having both high ion-exchange capacity and good physical toughness.

As described above, the membrane of the present invention is specific in having a carboxylic acid group density which is gradually decreased from the surface to the innerside, preferably at a gradient within a specific range. This is still another reason why the membrane of the present invention is by far more stable than the membrane of the prior art under more severe conditions than those conventionally used.

The membrane having a laminated structure comprising a membrane containing carboxylic acid groups and a membrane containing sulfonic acid groups, as disclosed by Japanese published unexamined patent applications No. 36589/1977 and No. 132089/1978, is incomplete in bonding as previously mentioned and liable to cause peel-off or water bubbles in a short period of time at the laminated portion.

On the other hand, according to the experience of the present inventors, even when the carboxylic acid density can be controlled to a certain extent in a membrane having carboxylic acid groups formed by chemical treatment, as disclosed by Japanese published unexamined patent applications No. 24176/1977, No. 104583/1978, No. 116287/1978 and 6887/1979, the resultant membrane is liable to cause peel-off or crack of the carboxylic acid layer, as compared with the membrane of the present invention, presumably due to the problem in polymeric structure as previously mentioned.

In contrast, as illustrated in the Examples, the membrane of the present invention can maintain stable performance for by far a longer time than the membranes of the prior art without causing abnormal phenomena such as peel-off or crack of the carboxylic acid layer even under the conditions of a high current density of 110 A/dm$^2$ and a high temperature of 95° C. or higher.

The membrane of the present invention may also have laminated, on one surface of the membrane with the lower carboxylic acid group density, a fluorinated cation exchange membrane consisting substantially of the units (C) as previously mentioned and the following recurring units (F):

$$(CF_2-CF)\phantom{xx}CF_3 \qquad\qquad (F)$$
$$\phantom{(CF_2-C}|\phantom{xx}|$$
$$\phantom{(CF_2}O-(CF_2CFO)_{p''}-(CF_2)_q-SO_3M$$

wherein p″=0 or 1, q is an integer of 3 to 5, M and has the same meaning as defined above, the ratio of recurring units being in the following range:

(C)/(F)<(C)/[(D)+(E)].

Such a structure is also preferred from the standpoint of lowering the electric resistance of a membrane. In this case, in order to obtain a membrane having lower electric resistance with physical toughness, it is preferred that p″ may be equal to zero and q equal to 1. It is also preferred that the thickness of the fluorinated cation exchange membrane comprising the recurring unit (F) may have a thickness ½ to 19/20 as thick as the entire membrane.

The membrane of the present invention may also be provided with a backing with a mechanical reinforcing material such as a net for the purpose of increasing the strength of the membrane. As such a backing material, a net made from polytetrafluoroethylene fibers is most suitable, but there may also be used a porous polytetrafluoroethylene sheet. It is also possible to incorporate fibrous polytetrafluoroethylene during molding of a membrane for increasing the strength thereof.

Referring now to the method for preparation of the membrane of the present invention, the membrane of the fluorinated copolymer used for preparation of the membrane of the present invention can be produced according to the method as previously described. Then, as the second step, a part or all of the terminal groups of the recurring unit (G) of a membrane prepared by the method as mentioned above comprising essentially the recurring units (C) and (G) as shown below:

$$(CF_2CF) \qquad\qquad (C)$$
$$\phantom{(CF_2C}|$$
$$\phantom{(CF_2C}L$$
(L is the same as defined above)

$$(CF_2-CF)\phantom{xx}CF_3 \qquad\qquad (G)$$
$$\phantom{(CF_2-C}|\phantom{xx}|$$
$$\phantom{(CF_2}O-(CF_2CFO)_k-(CF_2)_l-Z-R$$
(k, l, Z and R are the same as defined above)

are converted, if necessary, to sulfonylchloride groups —CF$_2$SO$_2$CL or sulfonylbromide groups —CF$_2$SO$_2$Br, preferably sulfonylchloride groups using a halogenating agent represented by the formula:

$B_2(AB_{d-2})_e$ wherein A is P; B is Cl or Br and d=3 or 5; and e=0 or 1. The reaction used in this step is different depending on the types of Z and R. Details of each reaction are set forth below for each type.

(a) When Z=—S—:

It is generally possible to react a halogen with a membrane for conversion to sulfonyl halide groups. From the standpoint of reactivity and ease of handling, chlorine may preferably be used. In this case, —CF$_2$SO$_2$Cl is formed directly or via —CF$_2$SCl. The reaction conditions may be variable within a broad range, but the reaction temperature is generally from 0° to 300° C. under normal pressure or under pressurization. The chlorine employed may either be in the dry state or in a solution dissolved in water, an organic solvent such as acetic acid, trichloroacetic acid, trifluoroacetic acid, or an inorganic solvent such as S$_2$Cl$_2$.

When Z=—S—, it may also be oxidized into sulfone of Z=—SO$_2$— or sulfoxide of Z=—SO—, using an oxidizing agent conventionally used such as ozone, conc.sulfuric acid, fuming sulfuric acid, nitric acid, sulfuryl chloride, hydrogen peroxide, potassium permanganate or potassium dichloromate. Said oxidation treatment may be conducted usually in an aqueous solution at 20° to 200° C., whereby an organic solvent such as acetic acid or trichloroacetic acid may also be present in the solution to accelerate permeation of the oxidizing agent into the membrane. The sulfoxide formed by the above oxidation treatment may be converted to —CF$_2$SO$_2$Cl with chlorine.

(b) When Z=—SO$_2$— (sulfone)

Conversion to sulfonylchloride groups is possible according to the method similar to that used in the case of Z=—S—. It may also be converted to sulfonic acid groups —CF$_2$SO$_3$M by hydrolysis with an alkali. The hydrolysis may be carried out using a solution of caustic soda or caustic potash dissolved in water, a mixed solvent of water with an organic solvent such as alcohol or dimethylsulfoxide, optionally containing an oxidizing agent added, for example, at 20° to 200° C.

The thus obtained sulfonic acid groups may easily be converted to sulfonylchloride groups by reaction with vapors of phosphorus pentachloride or a solution of phosphorus pentachloride dissolved in phosphorus oxychloride, an organic halide compound, etc. according to the method and the conditions as described in Japanese published unexamined patent applications No. 134888/1977 and No. 4289/1979. A mixture of phosphorus trichloride with chlorine may also be used.

Further, as the third step, a part or all of the sulfonyl halide groups at the terminal end of the recurring unit (H):

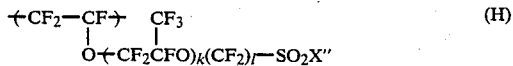 (H)

wherein k and l are the same as defined above, X" is Cl or Br, preferably Cl, are converted to carboxylic acid groups. From the standpoint of reactivity and ease in handling, it is most preferable to use sulfonylchloride groups.

Such a conversion can be accomplished by treatment of a membrane comprising the recurring units (C) and (H) with a reducing agent and according to the reaction method and reaction conditions as generally described in Japanese published unexamined patent applications No. 24176/1977, No. 24177/1977 and No. 132094/1978, thereby converting —CF$_2$— directly bonded to sulfur atom directly or via sulfinic acid groups into carboxylic acid groups. As the result, there is formed a specific structure of m=(l−1) in the pendant groups of the recurring units (E).

The reducing agents to be used in the present invention may preferably be selected from acids having reducing ability such as hydroiodic acid, hydrobromic acid, hypophosphorous acid, hydrogen sulfide water, arsenous acid, phosphorous acid, sulfurous acid, nitrous acid, formic acid, oxalic acid, etc., their metal salts, ammonium salts, and hydrazines, from the standpoint of reactivity and ease in handling. Among them, an inorganic acid having reducing ability is most preferred. These reducing agents may be used alone or, if necessary, as a mixture.

The structure of the membrane comprising carboxylic acid groups enriched on only one surface of the membrane, which is the excellent specific feature of the membrane according to the present invention, may be realized easily by applying the second step reaction or preferably the third step reaction on one surface of the membrane. In case of a membrane having a laminated structure, these reactions may be applied on the surface opposite to that on which lamination is effected.

The gradient of the carboxylic acid group density may be controlled to a desired shape of the density curve by adequately controlling various factors in the reactions in the second or the third step such as temperature, time, pressure, solvent composition, etc. to thereby balance the reaction rate and the diffusion velocity of a reagent into the membrane. For ease of control, it is preferred to effect such controlling in the third step.

As a preferable method for controlling the carboxylic acid group density, there may be mentioned a method wherein the above treatment with a reducing agent is effected in the presence of at least one organic compound having 1 to 12 carbon atoms selected from alcohols, carboxylic acids, sulfonic acids, nitriles or ethers, using especially a solution of said organic compounds dissolved in an aqueous reducing agent solution. In particular, carboxylic acids may preferably be used as such organic compounds. These organic compounds may be added in an amount, which is variable depending on the membrane employed, the reducing agent and organic compound employed as well as the reaction conditions and may suitably be selected within the range of 100 ppm or more.

Examples of alcohols to be used in the present invention may include methanol, ethanol, propanol, ethylene glycol, diethylene glycol, 1,4-butane diol, 1,8-octane diol, glycerine, and the like.

As typical examples of carboxylic acids and sulfonic acids, there may be mentioned formic acid, acetic acid, propionic acid, butyric acid, iso-butyric acid, n-valeric acid, caproic acid, n-heptanoic acid, caprylic acid, lauric acid, fluoroacetic acid, chloroacetic acid, bromoacetic acid, dichloroacetic acid, malonic acid, glutaric acid, trifluoroacetic acid, perfluoropropionic acid, perfluorobutyric acid, perfluorovaleric acid, perfluorocaproic acid, perfluoro-n-heptanoic acid, perfluorocaprylic acid, perfluoroglutaric acid, trifluoromethane sulfonic acid, perfluoroheptane sulfonic acid, methane sulfonic acid, ethane sulfonic acid, propane sulfonic acid, butane sulfonic acid, pentane sulfonic acid, hexane sulfonic acid, heptane sulfonic acid, and so on. Preferably, acetic acid, propionic acid, caprylic acid, trifluoroacetic acid, perfluorocaprylic acid or perfluorobutyric acid may be used.

Typical examples of nitriles are acetonitrile, propionitrile, adiponitrile, and the like. Ethers may be exemplified by diethylether, tetrahydrofuran, dioxane, ethylene glycol dimethylether, diethylene glycol dimethyl ether, etc. Among these organic compounds, some compounds may undergo chemical changes depending on the reducing agent employed and therefore it is desired to avoid such a combination.

The gradient of the carboxylic acid group density in the membrane may be determined, as illustrated in the Examples, by staining the cross-section of a membrane with a suitable dye and observing the result of staining, or alternatively by scraping the membrane substantially in parallel to the surface thereof (usually in a thickness of about 1 to 5 micron per each scraping), subjecting the scraped face to attenuated total reflection (hereinafter referred to as ATR) and calculating from the changes in intensity of the absorption peak based on the carboxylic acid groups.

In the membrane of the present invention or other fluorinated cation exchange membranes, the pendant structure having bonded ion-exchange groups can be identified by measurement of ATR or IR absorption spectrum after the reaction for elimination of ion-exchange groups.

Other than the method as described above wherein a reducing agent is used, there may also be used the same method as described in Japanese published unexamined patent application No. 125986/1978, wherein sulfonyl halide groups are once converted to —$CF_2I$, followed by conversion to carboxylic acid groups. Alternatively, the membrane comprising the recurring units (G) may be irradiated with ultra-violet rays or an electron beam to be directly converted to carboxylic acid groups. It is also possible to obtain a membrane containing carboxylic acid groups with more —$CF_2$— than that obtained by use of a reducing agent, i.e. m being greater than (l−1) in the pendant groups of the recurring unit (E), according to the method as described in Japanese published unexamined patent applications No. 104583/1978 and No. 116287/1978. Said method comprises reacting a membrane having sulfonyl halide groups or a membrane having sulfinic acid groups or —$CF_2I$ obtained as intermediate in the method as described above with a compound having carbonyl groups or unsaturated bonding under the conditions to eliminate $SO_2$ or iodine atom ionically or radically. According to these methods, however, it is very difficult to control the gradient of the carboxylic acid density; many steps are required for the reaction; the cost is high; expensive reagents are necessary; side reactions can be suppressed only with difficulty; pendant groups cannot be in the form of perfluoro groups; or the membrane may be damaged physically during the treatment. In any of these respects, any of said alternative methods is inferior to the method wherein a reducing agent is used. For this reason, in preparation of a membrane to be used under more severe conditions than those conventionally used, it is more preferable to use the method employing a reducing agent than those alternative methods as mentioned above.

The fourth step for preparation of the membrane of the present invention is to convert all of the residual sulfur containing terminal groups to sulfonic acid groups. This can easily be done according to the reaction as mentioned in the second step reaction or by application of the reactions such as oxidation, hydrolysis, etc. as described in Japanese published unexamined patent applications No. 24176/1977 and No. 24177/1977.

As apparently seen from the preparation methods as described above, the membrane of the present invention can be derived from common starting materials according to simple reactions to have carboxylic acid groups and sulfonic acid groups. Thus, the membrane can be manufactured easily and advantageously at low cost.

The cation exchange membrane according to the present invention may favorably be employed in electrolysis of an aqueous alkali metal halide solution. That is, the membrane of the present invention is useful not only in electrolysis of an alkali metal halide under conventional electrolysis conditions, i.e. a current density of 10 to 70 $A/dm^2$, a temperature of 20° to 100° C., alkali metal halide concentration of 1 to 5N and an alkali concentration of 1 to 15N, but is also useful under severe conditions, i.e. a current density of 70 to 200 $A/dm^2$ and a temperature of 100° to 150° C., with stable performance for a long time.

The sixth object of the present invention is to provide a novel fluorinated cation exchange membrane containing sulfonic acid groups, comprising essentially the following units (I) and (J):

 (I)

 (J)
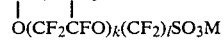

wherein k is 0 or 1, l is an integer of 3 to 5 and M is H, a metal or ammonium ion, the ratio of the numbers of the recurring units (I) and (J) being (I)/(J)=1.5 to 14. For the purpose of the present invention, it is preferred that the suffix k should be equal to zero. It is also preferred that the suffix l should be equal to 3 for ease in preparation of the monomer and a greater variable range of the polymer composition. A membrane with an l value of 6 or more is inferior to those with l values of 3 to 5 from the standpoint of difficulty in synthesis of the monomer and insufficient ion-exchange capacity obtained. Further, the ratio (I)/(J) may preferably in the range from 3 to 11, particularly preferably from 3.5 to 6.

The above sulfonic acid type cation exchange membrane can be prepared by use of the membrane of the aforesaid fluorinated copolymer as described above. Said membrane can be treated by application of the reactions as described above to convert all of the sulfur containing terminal groups into sulfonic acid groups to give the novel cation exchange membrane containing sulfonic acid groups comprising the recurring units (I) and (J) as defined above.

This membrane is useful in various fields such as electrolysis of an aqueous alkali metal halide solution, electrolysis of water, diaphragms for fuel cells, etc. For the reason mentioned below, this membrane is superior to fluorinated cation exchange membranes containing sulfonic acid groups conventionally used in commercial application.

The specific feature in performance of the sulfonic acid type membrane according to the present invention is based on the specific structure of the sulfur containing fluorinated vinylether of the following formula used for preparation of said sulfonic acid type membrane:

$$CF_2=CFO(CF_2\underset{|}{C}FO)_k-(CF_2)_l-Z-R$$
$$\phantom{CF_2=CFO(CF_2}CF_3\phantom{FO)_k-(CF_2)_l-Z-R}$$

wherein k, l, Z and R are the same as defined above.

The above monomer is different in the structure of the terminal end or in the number of members of the ring, as compared with the sulfur containing fluorinated vinylether of the formula:

$$CF_2=CFO\overline{(CF_2\underset{|}{C}FO)_{n'}}CF_2CF_2SO_2F$$
$$\phantom{CF_2=CFO(CF_2}CF_3\phantom{)_{n'}CF_2CF_2SO_2F}$$

wherein n' is 0 to 2, which is used as starting material for a sulfonic acid type membrane of the prior art, and therefore it is possible to form substantially no or to decrease to a great extent the cyclization reaction in the vinylization step as mentioned above. Thus, a monomer with k=0 can easily be prepared and there is also no deterioration of polymer properties due to cyclization during polymerization.

Accordingly, since it is possible to use a monomer with k=0 as principal starting material for preparation of a membrane, the resultant polymer can have a structure containing substantially no or only a very small proportion of pendant groups:

$$-CF_2\underset{|}{C}FO-.$$
$$\phantom{-CF_2}CF_3\phantom{FO-.}$$

Consequently, with the same level of the ion-exchange capacity, the content of fluorinated olefin can be increased. In other words, there can be produced a physically tough membrane with enhanced ion-exchange capacity.

Another reason why the membrane of the present invention is stable under severe conditions may be ascribed to the relative ratio of the recurring units (I) and (J), i.e. the ratio of (I)/(J) which is generally in the range from 1.5 to 14, preferably from 3 to 11, more preferably from 3.5 to 6. When said ratio is less than 1.5, the membrane is liable to swell during usage and therefore cannot maintain a stable performance for a long term. On the other hand, if it is greater than 14, the membrane is liable to shrink so as to make the electric resistance of the membrane impractically high.

The ion-exchange capacity of the membranes of the present invention may be represented by the following formula as being dependent on the structure of the recurring units, and the ratio of recurring units:

| | |
|---|---|
| Ion-exchange capacity = | 1000/[100r + (178 + 166k + 50l)] |
| | (meq/g-dry H-form resin) | wherein r=(I)/(J), k and l are the same as defined above.

In the prior art, the ion-exchange capacity of an ion-exchange membrane has been indicated in specific numerical values, as disclosed by Japanese published unexamined patent applications No. 120492/1975, No. 130495/1976, No. 36589/1977 and No. 24176/1977, and U.S. Pat. No. 4,065,366. According to the study by the present inventors, however, as noted above, the swelling and shrinking behavior of a membrane with a given species of ion-exchange groups is not controlled by the ion-exchange capacity per se of the membrane but by the most important factors including the fluorinated olefin constituting the copolymer, the copolymer ratio of the fluorinated vinylether having ion-exchange groups and the presence or absence or $$-CF_2\underset{|}{C}FO-.$$
$$\phantom{-CF_2}CF_3\phantom{FO-.}$$

In order to obtain a membrane having sufficiently low electric resistance and good physical toughness with small swelling or shrinking when used in electrolysis, it is required to use a fluorinated vinylether having no $$-CF_2\underset{|}{C}FO-$$
$$\phantom{-CF_2}CF_3\phantom{FO-}$$

group as principal component and to control the above copolymerization ratio within a certain range. The ion-exchange capacity as represented by the above formula is based on such considerations.

It is not clear why the above copolymerization ratio has such a decisive influence on the swelling and shrinking behavior of a membrane. For convenience of explanation, reference is made to a membrane containing the most preferred fluorinated olefin, i.e. tetrafluoroethylene. From analysis of X-ray diffraction of the membrane, tetrafluoroethylene seems to be partially crystallized. Since the degree of crystallization is greatly dependent on the above copolymerization ratio, it may be estimated that the crystallized region will function as quasi-crosslinks which control the swelling and shrinking behavior of the membrane.

In the membrane according to the present invention, it is possible to provide a structure containing substantially no or only a small amount of pendant groups:

$$-CF_2\underset{|}{C}FO-.$$
$$\phantom{-CF_2}CF_3\phantom{FO-.}$$

When a membrane with the same ion-exchange capacity is to be prepared, the copolymerization ratio of tetrafluoroethylene can be increased in the membrane of the present invention, as compared with a membrane prepared by use of $$CF_2=CFOCF_2\underset{|}{C}FOCF_2CF_2SO_2F$$
$$\phantom{CF_2=CFOCF_2}CF_3\phantom{FOCF_2CF_2SO_2F}$$

as a sulfur containing fluorinated vinylether, thereby providing a membrane having both high ion-exchange capacity and good physical toughness.

In the above sulfonic acid type membrane or other fluorinated cation exchange membranes, the pendant structure having bonded ion-exchange groups can be identified by measurement of ATR or IR absorption spectrum after the reaction for elimination of ion-exchange groups.

The fluorinated cation exchange membrane having sulfonic acid groups can be prepared from a membrane prepared by molding of a copolymer obtained by polymerization by converting the terminal groups of the recurring units (G) of a membrane prepared by the method as described above comprising essentially the recurring units (C) and (G) as shown below:

$$-(CF_2CF)-$$
$$\quad\ \ |$$
$$\quad\ \ L$$
(C)

(L is the same as defined above)

$$-(CF_2-CF)-\quad CF_3$$
$$\qquad |\qquad\quad |$$
$$\quad\ \ O-(CF_2CFO)_k-(CF_2)_l-Z-R$$
(G)

(k, l, Z and R are the same as defined above)

to sulfonylchloride groups —$CF_2SO_2Cl$ or sulfonylbromide groups —$CF_2SO_2Br$, preferably sulfonylchloride groups, using a halogenating agent represented by the formula:

$$B_2(AB_{d-2})_e$$

wherein A is P; B is Cl or Br and d=3 or 5 and e=0 or 1. The reaction used in this step may be carried out according to the method and under the conditions as already described.

The sulfonyl halide groups formed in the above method may readily be converted to sulfonic acid groups by hydrolysis with an alkali. In this case, the reaction may be accelerated by use of an organic solvent such as methanol, ethanol, dimethylsulfoxide, etc.

The thus prepared sulfonic acid type membrane can also be modified to have lower electric resistance by lamination with a membrane having greater exchange capacity or improved in physical strength by embedding a suitable reinforcing material, as previously described, with a membrane having both carboxylic acid groups and sulfonic acid groups.

The present invention is illustrated in further detail by referring to the following Examples, by which the present invention is not limited.

EXAMPLE 1

In a stainless steel autoclave of 3-liter capacity, there are charged 250 g of sodium ethyl mercaptide, 530 g of dimethyl carbonate and 750 g of tetrahydrofuran, and then the reaction system is brought into a reduced pressure of 50 to 60 mm Hg. While maintaining the temperature at 15° C. under vigorous agitation of the reaction system, tetrafluoroethylene is gradually blown into the system under reduced pressure. With the progress of the reaction, the rate of tetrafluoroethylene consumed is lowered until, finally at the tetrafluoroethylene pressure of 1 kg/cm², there is no more consumption of tetrafluoroethylene. After the reaction, the reaction mixture is neutralized with 300 g of 98% sulfuric acid. The sodium sulfate formed is filtered off and the filtrate is previously evaporated by an evaporator to remove tetrahydrofuran, followed by distillation of the residue, to obtain 520 g of the fraction of distillate at 84° C./30 mm Hg. Said fraction is found to have the structure of $C_2H_5SCF_2CF_2COOCH_3$ from elemental analysis, IR and NMR spectra.

IR characteristic absorption (liquid): 2960, 2930, 2870 cm$^{-1}$($C_2H_5$—), 1780 cm$^{-1}$(—$CO_2$—), 1300–1100 cm$^{-1}$(—$CF_2$—).

Elemental analysis: $C_6H_8F_4O_2S$: Calculated: C, 32.7; H, 3.6; F, 34.5; S, 14.5. Found: C, 32.2; H, 3.9; F, 33.9; S, 14.3.

EXAMPLE 2

While heating 100 g of the compound $C_2H_5SCF_2CF_2COOCH_3$ obtained in Example 1 at 50° C., an aqueous 10N caustic soda solution is added gradually dropwise thereto and the dropwise addition is continued until the reaction system is weakly alkaline to convert said compound into $C_2H_5SCF_2CF_2CO_2Na$. After removing sufficiently the methanol formed in the reaction system by an evaporator, the reaction system is made weakly acidic by addition of conc. sulfuric acid. From the reaction system separated into two layers, the organic layer comprising $C_2H_5SCF_2CF_2CO_2H$ is separated, followed by thorough drying of said organic layer. In a stainless steel autoclave, there are charged 80 g of $C_2H_5SCF_2CF_2CO_2H$, 40 cc of 1,1,2-trichloro-1,2,2-trifluoroethane and 32 g of sodium fluoride, and then 63 g of sulfur tetrafluoride is pressurized into said autoclave. While stirring the mixture, the reaction is carried out at 80° C. for 4 hours. After completion of the reaction, gas purge is effected with dry nitrogen and sodium fluoride is filtered off from the reaction mixture. The filtrate is subjected to distillation to give 54 g of the fraction of distillate at 46° C./100 mm Hg.

Said fraction is identified by elemental analysis, IR and NMR spectra to have the structure of $C_2H_5SCF_2CF_2COF$.

IR characteristic absorption (liquid): 2960, 2930, 2870 cm$^{-1}$($C_2H_5$), 1880 cm$^{-1}$(—COF), 1300–1100 cm$^{-1}$(—$CF_2$—).

Elemental analysis values: $C_5H_5F_5OS$: Calculated: C, 28.8; H, 2.4; F, 45.7; S, 15.4. Found: C, 29.0; H, 2.6; F, 45.2; S, 15.3.

EXAMPLE 3

The compound $C_2H_5SCF_2CF_2CO_2H$ (80 g) prepared, in Example 2, by subjecting the compound $C_2H_5SCF_2CF_2COOCH_3$ to the alkali treatment and to the conc. sulfuric acid treatment, is mixed with 400 ml of a mixture (2:1, volume ratio) of 30% aqueous hydrogen peroxide solution and glacial acetic acid. The reaction is carried out with stirring at 90° C. for 5 hours.

To the resultant reaction mixture, there is added conc. sulfuric acid to separate the mixture into two layers, from which the organic layer comprising $C_2H_5SO_2CF_2CF_2CO_2H$ is separated. To this layer is added methanol under acidic conditions, and the reaction is conducted at 60° C. for 3 hours. Then, the reaction mixture is subjected to distillation to give 70 g of the fraction of distillate at 183°–186° C./40 mm Hg. Said fraction is identified by elemental analysis, IR and NMR spectra to have the structure of $C_2H_5SO_2CF_2CF_2COOCH_3$.

IR characteristic absorption (liquid): 2960, 2930, 2870 cm$^{-1}$(—$C_2H_5$), 1780 cm$^{-1}$(—$CO_2$—), 1360 cm$^{-1}$(—$SO_2$—), 1300–1100 cm$^{-1}$(—$CF_2$—).

Elemental analysis values: $C_6H_8F_4O_4S$: Calculated: C, 28.6; H, 3.2; F, 30.2; S, 12.7. Found: C, 28.3; H, 3.6; F, 29.7; S, 12.9.

EXAMPLE 4

After drying thoroughly the organic layer comprising $C_2H_5SO_2CF_2CF_2CO_2H$ prepared in Example 3, 100 g of said organic layer, 50 cc of 1,1,2-trichloro-1,2,2-trifluoroethane and 40 g of sodium fluoride are charged into an autoclave of 500 ml capacity, followed by pressurization of 100 g of sulfur tetrafluoride thereinto. While stirring the mixture, the reaction is carried out at 80° C. for 6 hours. After the reaction is over, dry nitrogen is flushed for gas purge and sodium fluoride is filtered off from the reaction mixture. Distillation of the filtrate gives 90 g of the fraction of distillate at 59°–65° C./13 mm Hg.

Said fraction is identified by elemental analysis, IR and NMR spectra to have the structure of $C_2H_5SO_2CF_2CF_2COF$.

IR characteristic absorption (liquid): 2960, 2930, 2870 $cm^{-1}(-C_2H_5)$, 1880 $cm^{-1}(-COF)$, 1360 $cm^{-1}(-SO_2-)$, 1300–1100 $cm^{-1}(-CF_2-)$.

Elemental analysis values: $C_5H_5F_5O_3S$: Calculated: C, 25.0; H, 2.1; F, 39.6; S, 13.3. Found: C, 25.5; H, 1.8; F, 39.2; S, 13.1.

EXAMPLE 5

In a stainless steel autoclave of 3-liter capacity, there are charged 280 g of sodium methyl mercaptide, 530 g of dimethyl carbonate and 1000 g of tetrahydrofuran, and then the reaction system is brought into a reduced pressure of 50 to 60 mm Hg. While vigorously agitating the reaction system and maintaining the temperature at 10° C., tetrafluoroethylene is gradually blown into the system under reduced pressure. With progress of the reaction, the rate of tetrafluoroethylene consumed is lowered. Finally, at the tetrafluoroethylene pressure of 1 kg/cm$^2$, there is no more consumption of tetrafluoroethylene. After the reaction, the reaction mixture is neutralized with 380 g of conc. sulfuric acid(98%). The sodium sulfate formed is filtered off and the filtrate is previously evaporated by an evaporator to remove tetrahydrofuran. Distillation of the residue gives 660 g of the fraction of distillate at 83° C./50 mm Hg.

Said fraction is identified by elemental analysis, IR and NMR spectra to have the structure of $CH_3SCF_2CF_2COOCH_3$.

IR characteristic absorption (liquid): 3025, 2970, 2850 $cm^{-1}(CH_3-)$, 1780 $cm^{-1}(-CO_2-)$, 1300–1100 $cm^{-1}(-CF_2-)$.

Elemental analysis values: $C_5H_6F_4O_2S$: Calculated: C, 29.1; H, 2.9; F, 36.9; S, 15.5. Found: C, 29.5; H, 2.4; F, 36.1; S, 15.7.

EXAMPLE 6

While heating 100 g of the compound $CH_3SCF_2CF_2COOCH_3$ at 50° C., 10N-aqueous caustic soda solution is added gradually dropwise until the reaction system is weakly alkaline to convert said compound to $CH_3SCF_2CF_2CO_2Na$. After complete removal of the methanol formed in the reaction system, conc. sulfuric acid is added to the reaction system to make it acidic. From the reaction system separated into two layers, the organic layer comprising $CH_3SCF_2CF_2CO_2H$ is separated and said organic layer is thoroughly dried. In an autoclave of stainless steel, there are charged 80 g of $CH_3SCF_2CF_2CO_2H$, 40 cc of 1,1,2-trichloro-1,2,2-trifluoroethane and 32 g of sodium fluoride, and then 65 g of sulfur tetrafluoride is pressurized into said autoclave. While stirring the mixture, the reaction is carried out at 80° C. for 4 hours. After the reaction is over, dry nitrogen is flushed for gas purge and the reaction mixture is filtered to remove sodium fluoride. The filtrate is distilled to give 57 g of the fraction of distillate at 74°–76° C. Said fraction is identified by elemental analysis, IR and NMR spectra to have the structure of $CH_3SCF_2CF_2COF$.

IR characteristic absorption (liquid): 3025, 2970, 2850 $cm^{-1}(CH_3-)$, 1880 $cm^{-1}(-COF)$, 1300–1100 $cm^{-1}(-CF_2-)$.

Elemental analysis values: $C_4H_3F_5OS$: Calculated: C, 24.7; H, 1.5; F, 49.0; S, 16.5. Found: C, 24.9; H, 1.8; F, 48.2; S, 16.3.

EXAMPLE 7

The compound $CH_3SCF_2CF_2COOH$ (100 g) prepared, in Example 6, by saponifying $CH_3SCF_2CF_2COOCH_3$, followed by acid treatment and drying treatment, is introduced into a reactor. While maintaining the temperature in the reactor at 80° to 85° C. under vigorous agitation, there are gradually added drops of a mixture (60 cc) of thionyl chloride-dimethylformamide(thionyl chloride/dimethylformamide=20/1, volume ratio). After completion of the dropwise addition, the reaction is continued until generation of hydrogen chloride gas is terminated. On termination of hydrogen chloride gas generation, the reaction mixture is distilled to give 110 g of the fraction of distillate boiling at 103°–105° C. (principally composed of $CH_3SCF_2CF_2COCl$).

In a reactor, there are charged 140 g of NaF and 100 cc of dry tetramethylene sulfone. After heating the mixture to 85° C., under vigorous agitation, the above $CH_3SCF_2CF_2COCl$ (110 g) is added gradually dropwise into the mixture. After the reaction has continued for one hour, a vacuum line equipped with a cooling trap is connected to the reactor to reduce the pressure in the reactor to 10 mm Hg and heating is effected at 100° C. for 30 minutes. The condensed liquid product in the trap is distilled to give 80 g of the fraction of distillate at 74°–76° C.

Said fraction is identified by elemental analysis, IR and NMR spectra to have the structure of $CH_3SCF_2CF_2COF$.

IR characteristic absorption (liquid): 3025, 2970, 2850 $cm^{-1}(CH_3-)$, 1880 $cm^{-1}(-COF)$, 1300–1100 $cm^{-1}(-CF_2-)$.

Elemental analysis values: $C_4H_3F_5OS$: Calculated: C, 24.7; H, 1.5; F, 49.0; S, 16.5. Found: C, 24.5; H, 1.7; F, 48.6; S, 16.9.

EXAMPLE 8

The compound $C_2H_5SCF_2CF_2COOCH_3$ prepared in Example 1 (330 g) is added dropwise at room temperature over one hour, while under vigorous agitation, into a reactor wherein chlorine gas (500 ml/minute) is previously passed through trifluoroacetic acid (100 ml). After said dropwise addition, the reaction mixture is left to stand for 10 hours, followed by distillation of the product and collection of the fraction of distillate at 70°–75° C./60 mm Hg to give 310 g of said fraction of distillate.

Said fraction is identified by elemental analysis, IR spectrum, NMR spectrum and to have the formula $ClSCF_2CF_2CO_2CH_3$.

Elemental analysis values: Found: C, 21.4; H, 1.2; F, 33.1; S, 13.9. Calculated (for $C_4H_3F_4SO_2Cl$): C, 21.2; H, 1.3; F, 33.5; S, 14.1.

EXAMPLE 9

While passing chlorine gas at the rate of 500 ml/minute into a cold water (200 ml) previously saturated with chlorine, under vigorous agitation, the sulphenyl chloride prepared in Example 8 (226.3 g) is added gradually thereto. After the addition is completed, the reaction is continued for an additional 5 hours. Then, the lower layer is taken out to obtain 232 g of the fraction of distillate at 80°–82° C. under 60 mm Hg.

Said fraction is identified by IR spectrum, elemental analysis and NMR spectrum to have the structure of $ClSO_2CF_2CF_2CO_2CH_3$.

IR absorption spectrum: 1415 cm$^{-1}$

1785 cm$^{-1}$(—COOCH$_3$), 2960 cm$^{-1}$(—CH$_3$).

Elemental analysis: Found: C, 18.7; H, 1.0; F, 29.1; S, 12.6. Calculated (for $C_4H_3F_4SO_4Cl$): C, 18.6, H, 1.2, F, 29.4; S, 12.4.

EXAMPLE 10

The perfluoro-3-chlorosulfonylmethyl propionate (258.5 g) obtained in Example 9 is neutralized with 8N-NaOH, followed by removal of water and methanol.

After the residue is dried, phosphorus pentachloride (312 g) and phosphorus oxychloride (150 g) are added thereto and the reaction is carried out under reflux on a heating bath at 130° C. for 10 hours. After the reaction, distillation of the product gives 220 g of the fraction of distillate at 70° C. under 100 mm Hg.

This substance is identified by IR absorption spectrum, elemental analysis and NMR spectrum to be $ClSO_2CF_2CF_2COCl$ (perfluoro-3-chlorosulfonylpropionyl chloride).

IR absorption spectrum: 1790 cm$^{-1}$(—COCl), 1415 cm$^{-1}$(—SO$_2$Cl).

Elemental analysis: Found: C, 13.4; F, 28.5; S, 12.1; Cl, 27.3. Calculated (for $C_3F_4SO_3Cl_2$): C, 13.7; F, 28.9; S, 12.2; Cl, 27.0.

EXAMPLE 11

In a stainless steel autoclave of 500 cc capacity equipped with a gas blowing inlet, there are charged 100 g of the compound $C_2H_5SCF_2CF_2COF$ prepared similarly as in in Example 2, 120 g of tetraglyme(tetraethyleneglycol dimethylether) and 75 g of dry CsF. After the mixture is left to stand at room temperature for 16 hours, 80 g of hexafluoropropylene oxide (hereinafter referred to as HFPO) is blown into the autoclave while maintaining the temperature at 30° C., gradually while maintaining the pressure at 1.5 kg/cm$^2$ or lower. After a predetermined amount of HFPO is blown into the autoclave, stirring is conducted to a constant pressure and unaltered HFPO is thereafter removed. The residue is subjected to distillation, whereby 70 g of the fraction of distillate at 84°–87° C./100 mm Hg is obtained. The fraction is found to have the structure of

as identified by elemental analysis, IR and NMR spectra.

IR (liquid): 2960, 2930, 2870 cm$^{-1}$(—C$_2$H$_5$), 1880 cm$^{-1}$(—COF), 1100–1300 cm$^{-1}$(—CF$_2$—).

Elemental analysis: $C_8H_5F_{11}O_2S$: Calculated: C, 25.7, H, 1.3; F, 55.9; S, 8.6. Found: C, 26.1; H, 1.5; F, 54.8; S, 8.7.

EXAMPLE 12

The reaction is conducted under the same conditions as in Example 11 except that the amount of HFPO is changed to 160 g and the reaction temperature to −10° C. After the reaction, distillation of the product is carried out to give the following fractions of distillate:

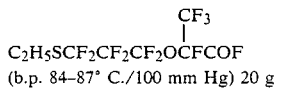
(b.p. 84–87° C./100 mm Hg) 20 g

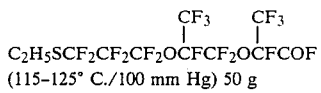
(115–125° C./100 mm Hg) 50 g

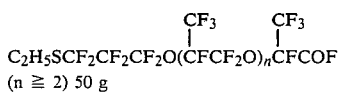
(n ≧ 2) 50 g

The structure of each fraction of distillate is identified by IR spectra and measurement of molecular weight by titration.

EXAMPLE 13

When the same procedure as in Example 11 is repeated except for using 100 g of $C_2H_5SO_2CF_2CF_2COF$ as prepared in Example 4 in place of $C_2H_5SCF_2CF_2COF$, there is obtained 50 g of the fraction of distillate at 90°–95° C./10 mm Hg. Said fraction is identified by elemental analysis, IR and NMR spectra to have the structure of

IR (liquid): 2960, 2930, 2870 cm$^{-1}$(—C$_2$H$_5$), 1880 cm$^{-1}$(—COF), 1360 cm$^{-1}$(—SO$_2$—), 1100–1300 cm$^{-1}$(—CF$_2$—).

Elemental analysis: $C_8H_5F_{11}O_4S$: Calculated: C, 23.6; H, 1.2; F, 51.5; S, 7.9. Found: C, 24.0; H, 1.4; F, 50.4; S, 8.0.

EXAMPLE 14

In a 500 cc autoclave made of stainless steel equipped with a gas blowing inlet, there are charged 100 g of the compound $CH_3SCF_2CF_2COF$ prepared in Example 7, 57 g of tetraglyme(tetraethyleneglycol dimethylether) and 39 g of CsF. After the mixture is left to stand at room temperature with stirring for 16 hours, 104 g of hexafluoropropylene oxide (hereinafter referred to as HFPO) is blown into the autoclave gradually while maintaining the pressure at 1.5 kg/cm$^2$ or lower, while maintaining the temperature at 5° C. After a predetermined amount of HFPO is charged, stirring is conducted to a constant pressure and then unaltered HFPO is removed. After separating CsF from the reaction mixture by filtration, the filtrate is distilled to give 65 g of the fraction of distillate at 69°–72° C./100 mm Hg. Said fraction is identified by elemental analysis, IR and NMR spectra to have the structure of

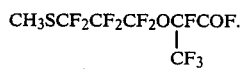

IR characteristic absorption (liquid): 3025, 2970, 2850 cm$^{-1}$(—CH$_3$), 1880 cm$^{-1}$(—COF), 1300-1100 cm$^{-1}$(—CF$_2$—).

Elemental analysis: C$_7$H$_3$F$_{11}$O$_2$S: Calculated: C, 23.3; H, 0.8; F, 58.1; S, 8.9. Found: C, 23.7; H, 1.0; F, 57.3; S, 9.1.

EXAMPLE 15

A tubular reactor made of stainless steel having a diameter of 3 cm and a length of 30 cm is filled with 100 cc of Na$_2$CO$_3$. While passing dry nitrogen through the reactor at the rate of 250 cc/min., the filler bed is heated externally by means of an electric heater at 350° C. to be preliminarily dried. After preliminary drying is continued for 4 hours, the rate of dry nitrogen passed is changed to 50 cc/min. and, while maintaining the filler bed at 185° to 190° C., the compound

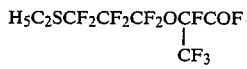

(120 g) as prepared in Example 11 is fed into the tubular reactor at the rate of 30 g/hr. The vapor emitted from the bottom of the tube is condensed and collected in a trap cooled by dry ice-methanol. The liquid composition is distilled to obtain 70 g of the fraction of distillate at 77°-80° C./100 mm Hg.

Said fraction is identified by elemental analysis, IR and NMR spectra to have the structure of H$_5$C$_2$SCF$_2$CF$_2$CF$_2$OCF=CF$_2$.

IR (liquid): 2960, 2930, 2870 cm$^{-1}$(C$_2$H$_5$—), 1840 cm$^{-1}$(CF$_2$=CFO—), 1100-1300 cm$^{-1}$(—CF$_2$—).

Elemental analysis: C$_7$H$_5$F$_9$OS: Calculated: C, 27.3; H, 1.6; F, 55.5; S, 10.4. Found: C, 27.1; H, 1.8; F, 55.0; S, 10.3.

EXAMPLE 16

Example 15 is repeated except that the compound

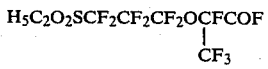

(120 g) prepared in Example 13 is used in place of the compound

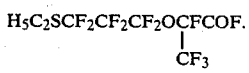

As the result, distillation of the reaction product gives 50 g of the fraction of distillate boiling at 82°-86° C./10 mm Hg. Said fraction is identified by elemental analysis, IR and NMR spectra to have the structure of H$_5$C$_2$O$_2$SCF$_2$CF$_2$CF$_2$OCF=CF$_2$.

IR (liquid): 2960, 2930, 2870 cm$^{-1}$(C$_2$H$_5$—), 1840 cm$^{-1}$(CF$_2$=CFO—), 1360 cm$^{-1}$(SO$_2$), 1100-1300 cm$^{-1}$(—CF$_2$—).

Elemental analysis: C$_7$H$_5$F$_9$O$_3$S: Calculated: C, 24.7; H, 1.5; F, 50.3; S, 9.4. Found: C, 25.1; H, 1.7; F, 49.3; S, 9.6.

EXAMPLE 17

The compound

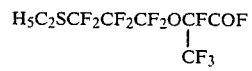

as prepared in Example 11 is subjected to hydrolysis with an excess of an aqueous NaOH solution, followed by dehydration. The solid residue is washed several times with acetone to effect extraction of the sodium carboxylate. The extract is evaporated by an evaporator to remove acetone. The solid product is crushed and thoroughly dried under reduced pressure at 100° C. to obtain

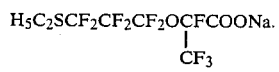

A round-bottomed glass flask of 500 cc capacity is equipped with a stirrer, a heater and an outlet for effluent gas which is connected via a trap cooled by dry ice-methanol to a vacuum line. In said flask, there is charged 100 g of

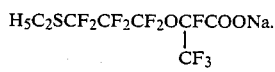

While maintaining the inner pressure at 10 mm Hg under stirring, said compound is thermally decomposed at 200° C. for 2 hours. The condensed liquid in the trap is subjected to precision distillation to obtain 18 g of the fraction of distillate at 77°-80° C./100 mm Hg. Said fraction is identified by elemental analysis, IR and NMR spectra to have the structure of H$_5$C$_2$SCF$_2$CF$_2$CF$_2$OCF=CF$_2$.

EXAMPLE 18

Example 15 is repeated except that the compound

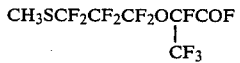

as prepared in Example 14 is used in place of

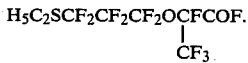

As the result, there is obtained 65 g of the fraction of distillate boiling at 81° C./200 mm Hg.

Said fraction is identified by elemental analysis, IR and NMR spectra to have the structure of CH$_3$SCF$_2$CF$_2$CF$_2$OCF=CF$_2$.

IR characteristic absorption (liquid): 3025, 2970, 2850 cm$^{-1}$(—CH$_3$), 1840 cm$^{-1}$(CF$_2$=CFO—), 1300-1100 cm$^{-1}$(—CF$_2$—).

Elemental analysis: C$_6$H$_3$F$_9$OS: Calculated: C, 24.5; H, 1.0; F, 58.2; S, 10.9. Found: C, 24.2; H, 1.2; F, 57.5; S, 11.1.

COMPARATIVE EXAMPLE 1

The procedure of Example 15 is repeated except that

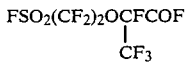

is used and passed through the sodium carbonate bed in place of

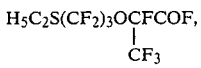

whereby no objective $CF_2\!=\!CFO(CF_2)_2SO_2F$ is obtained but only the cyclized product

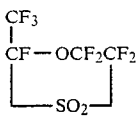

can be obtained.

EXAMPLE 19

In a stainless steel autoclave of 300 cc capacity, there are charged 10 g of $CF_2\!=\!CFO(CF_2)_3SC_2H_5$, 0.1 g of ammonium persulfate and water. The mixture is emulsified using ammonium perfluorooctanoate as emulsifier and polymerized at 50° C. under the pressure of 15 kg/cm$^2$ of tetrafluoroethylene, while adding sodium hydrogen sulfite as co-catalyst, to prepare the copolymer of the present invention. As the result of elemental analysis, this copolymer is found to contain 4.23% of sulfur.

This copolymer is formed into a thin film for measurement of attenuated total reflection (ATR). As the result of measurement, there are found absorptions at 2980 cm$^{-1}$ due to ethyl group, 990 cm$^{-1}$ due to ether group and 740 cm$^{-1}$ due to C-S-C.

The above copolymer is found to have a melt index of 1.6 g/10 min., as measured under the conditions of the temperature of 250° C. and the load of 2.16 kg by means of a device with an orifice of 2.1 mm in diameter and 8 mm in length.

This copolymer is formed into a film with a thickness of 250μ and treated with chlorine gas at 120° C. for 20 hours, followed further by treatment with a saturated aqueous chlorine water at 83° C. for 20 hours. The resultant film is subjected to measurement of ATR, whereby the absorption by ethyl groups at around 3000 cm$^{-1}$ is found to be vanished and instead thereof there appears absorption due to sulfonyl chloride groups at around 1420 cm$^{-1}$. The ion-exchange capacity is measured after hydrolyzing a part of said film with an alkali to be 1.3 meq/g-dry resin, indicating that the ratio of the recurring units, i.e.

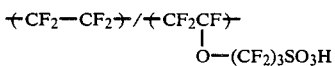

is 4.4.

One surface of this film having sulfonyl chloride groups is treated with a mixture comprising 57% hydroiodic acid and glacial acetic acid at a volume ratio of 15:1 at 72° C. for 18 hours and then hydrolyzed with an alkali. Furthermore, the thus treated membrane is treated with an aqueous 5% sodium hypochlorite solution at 90° C. for 16 hours to obtain a cation exchange membrane. Measurement of the ATR of this membrane gives the result that there are observed absorptions at 1690 cm$^{-1}$ due to carboxylic acid salt form and at 1060 cm$^{-1}$ due to sulfonic acid salt form. When the cross-section of the membrane is stained with an aqueous Malachite Green solution adjusted at pH=2, the membrane is stained in blue to the depth of 12μ from the treated surface, the residual portion being stained in yellow. The gradient of carboxylic acid density in the layer stained in blue is measured according to the following method.

According to the method similar to that described above, there is prepared a membrane having the same exchange capacity wherein all the ion-exchange groups are converted to carboxylic acid groups. The ATR of this membrane is measured and absorbance of carboxylic acid salt at 1690 cm$^{-1}$ is calculated according to the base line method, said absorbance being determined as 100. The surface layer on the side having carboxylic acid salt groups of the aforesaid membrane is scraped evenly and the scraped surface is subjected to measurement of ATR, from which the absorbance of the carboxylic acid salt is calculated. The percentage A % is calculated based on the absorbance of the film of the above membrane containing only carboxylic acid groups. On the other hand, the thicknesses before and after scraping are measured to determine the difference Bμ therebetween. Thus, the density of carboxylic acid groups in the thickness of Bμ from the surface layer is determined as A %.

The densities of carboxylic acid groups in the membrane of this Example as found in the scraped sections are 100% on the surface, 88% at the depth of 5μ from the surface, 68% at the depth of 10μ, 46% at the depth of 15μ, 26% at the depth of 20μ and 0% at the depth of 29μ. The accompanying drawing shows the relation between the depth and the density, indicating the maximum density gradient of 4.4%/μ.

The electrolysis performance of said membrane is measured according to the following method.

There is used an electrolytic cell comprising the anode compartment and the cathode compartment separated by said membrane with a current passage area of 0.06 dm$^2$ (2 cm×3 cm) and said membrane is assembled in the cell so that the surface having carboxylic acid groups may face toward the cathode side. As the anode, a dimensionally stable metal electrode is used and as the cathode an iron plate. Into the anode compartment is charged a saturated aqueous sodium chloride solution and the pH of the anolyte is maintained at 3 by the addition of hyrochloric acid. While 10N aqueous caustic soda solution is circulated to the cathode compartment, water is added thereto in order to maintain the concentration at a constant value.

While maintaining the temperature in both the anode compartment and the cathode compartment at 95° C., current is passed at the current density of 110 A/dm$^2$. The current efficiency is calculated by dividing the amount of caustic soda formed in the cathode compartment by the theoretical amount calculated from the quantity of current passed.

The current efficiency and the cell voltage are measured with lapse of time to obtain the following results:

| | | |
|---|---|---|
| Current passage time (hrs.): | 24 | 720 |
| Current efficiency (%): | 93 | 93 |

| -continued | | |
|---|---|---|
| Voltage (V): | 4.7 | 4.7 |

After passage of current, the membrane is observed to have no physical damage such as water bubbles, cracks or peel-off.

COMPARATIVE EXAMPLE 2

In a stainless steel autoclave of 300 cc capacity, there are charged 10 g of

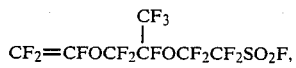

0.1 g of ammonium persulfate and water. The mixutre is emulsified using ammonium perfluorooctanoate as emulsifier and polymerized at 50° C. under the pressure of tetrafluoroethylene of 3 kg/cm², while adding sodium hydrogen sulfite as co-catalyst. The ion-exchange capacity of the resultant copolymer is measured after hydrolysis of a part thereof to be 1.3 meq/g-dry resin. The ratio of the recurring units of this polymer, i.e.

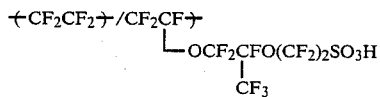

is found to be 3.3.

After washing the above polymer with water, the polymer is formed into a film with a thickness of 250μ, which is in turn hydrolyzed with an alkali. The resultant membrane is too low in mechanical strength to perform an evaluation thereof.

COMPARATIVE EXAMPLE 3

Comparative example 2 is repeated except that the pressure of tetrafluoroethylene is changed to 5 kg/cm². The resultant polymer is found to have an ion-exchange capacity of 0.89 meq/g-dry resin. Said polymer is found to have a ratio of the recurring units, namely

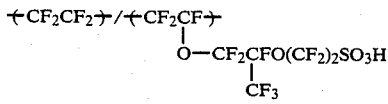

of 6.8.

After the above polymer is washed with water, it is molded into a film with a thickness of 250μ and then hydrolyzed with an alkali. This film is thoroughly dried and then treated at 110° C. for 20 hours by immersing said film in a mixture comprising phosphorus pentachloride and phosphorus oxychloride at a weight ratio of 1:3. By measurement of the ATR of this membrane, there appears specific absorption at 1420 cm⁻¹ due to sulfonyl chloride groups. After treatment of one surface of said membrane with 57% hydroiodic acid at 83° C. for 20 hours, the treated surface is hydrolyzed with an alkali, followed further by treatment with an aqueous 5% sodium hypochlorite solution at 90° C. for 16 hours. By measurement of the ATR of the membrane, there is observed specific absorption at 1690 cm⁻¹ on the treated surface due to carboxylic acid salt. When the cross-section of the membrane is stained similarly as in Example 19, the membrane is found to be stained in blue to the depth of 8.6μ from the surface, the residual portion being stained in yellow.

This membrane is provided for electrolysis evaluation according to the same method as described in Example 19, with the surface having carboxylic acid groups facing toward the cathode side. The current efficiency and the voltage are measured to give the following results:

| Current passage time (hrs.): | 24 | 720 |
|---|---|---|
| Current efficiency (%): | 94 | 86 |
| Voltage (V): | 5.6 | 6.1 |

After passage of current, the membrane surface subjected to current passage is observed to find that there are water bubbles. The cross-section of the membrane is also observed to find that there is peel-off in the carboxylic acid layer at the depth of 5μ from the surface layer.

COMPARATIVE EXAMPLE 4

Polymerization is conducted in the same manner as in Comparative example 2 except that the pressure of tetrafluoroethylene is changed to 5 kg/cm². A part of the resultant polymer is hydrolyzed to give an ion-exchange resin having an ion-exchange capacity of 0.83 meq/g-dry resin. This polymer is molded into a film with a thickness of 50μ. This film is called film a.

On the other hand, 16 g of CF$_2$=CFO(CF$_2$)$_3$COOCH$_3$, 0.17 g of ammonium persulfate and water are charged into a stainless steel autoclave of 500 cc capacity. The mixture is emulsified using ammonium perfluorooctanoate as emulsifier and polymerization is carried out at 50° C. under the pressure of tetrafluoroethylene of 7 kg/cm² using sodium hydrogen sulfite as co-catalyst. A part of the polymer is subjected to hydrolysis and the hydrolyzed product is found to have an ion-exchange capacity of 1.10 meq/g-dry resin. This polymer is molded into a film with a thickness of 100μ. This film is called film b.

The film a is placed on the film b and the resultant composite is subjected to press molding to give a laminated membrane. This membrane, after hydrolysis with an alkali, is evaluated for its electrolysis performance with the surface of the film b facing toward the cathode side. The results are shown below:

| Current passage time (hrs.): | 24 | 720 |
|---|---|---|
| Current efficiency (%): | 92 | 84 |
| Voltage (V): | 18 | 20 |

After passage of current, the membrane subjected to the passage of current is found to have water bubbles formed on the entire surface. By observation of the cross-section of the membrane, there is found peel-off at exactly the interface between the film a and the film b.

COMPARATIVE EXAMPLE 5

Example 19 is repeated except that

and CF$_2$=CFO(CF$_2$)$_4$COOH$_3$ are used in place of CF$_2$=CFOCF$_2$CF$_2$CF$_2$SC$_2$H$_5$ and copolymerization is carried out while blowing tetrafluoroethylene according to the method as described in Example 2 of Japanese published unexamined patent application No. 120492/1975. This polymer is molded into a film with a thickness of 250μ and, after hydrolysis with an alkali, evaluated for its electrolysis performance according to the method as described in Example 19. The results are shown below.

| Current passage time (hrs.): | 24 | 720 |
|---|---|---|
| Current efficiency (%): | 89 | 82 |
| Voltage (V): | 4.5 | 4.4 |

COMPARATIVE EXAMPLE 6

One surface of the sulfonyl chloride type membrane obtained in Comparative example 3 is treated with a perfluoro-dimethylcyclobutane solution containing 5 wt.% of $CF_2=CFO(CF_2)_3COOCH_3$ and a catalytic amount of azobisisobutyronitrile at 50°–60° C. for 5 hours. After said treatment, the membrane is subjected to hydrolysis treatment with 2.5N caustic soda/50% aqueous methanol solution. As the result of measurement of the ATR of the treated surface, there is found specific absorption of carboxylic acid salt at 1690 cm$^{-1}$. When the cross-section of the membrane is stained with Malachite Green, the layer with the thickness of 4μ from the treated surface is found to be stained in blue.

Evaluation of electrolysis performance of the membrane is performed similarly as in Example 19, with the surface having carboxylic acid groups facing toward the cathode side, to give the following results.

| Current passage time (hrs.): | 24 | 720 |
|---|---|---|
| Current efficiency (%): | 91 | 80 |
| Voltage (V): | 5.7 | 6.2 |

The membrane surface subjected to current passage is found to have water bubbles formed on its entire surface.

COMPARATIVE EXAMPLE 7

According to the method similar to Comparative example 4, there are prepared a copolymer a of tetrafluoroethylene with

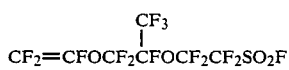
$$CF_2=CFOCF_2CFOCF_2CF_2SO_2F$$

(ion-exchange capacity after hydrolysis=0.91 meq/g-dry resin) and a copolymer b of tetrafluoroethylene with

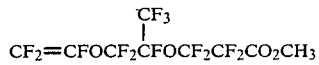
$$CF_2=CFOCF_2CFOCF_2CF_2CO_2CH_3$$

(ion-exchange capacity after hydrolysis=0.92 meq/g-dry resin). The copolymers a and b are blended at a weight ratio of 50/50 on a roll mill and then press molded into a film of 100μ in thickness. This film is called film A. Separately, the copolymer a is press molded into a film of 100μ in thickness. This film is called film B. The films A and B are placed on each other and press molded into a laminated membrane. This membrane is subjected to hydrolysis with an alkali and thereafter its electrolysis performance is measured similarly as in Example 19, with the surface of the film A facing toward the cathode side. The results are shown below.

| Current passage time (hrs.): | 24 | 720 |
|---|---|---|
| Current efficiency (%): | 90 | 82 |
| Voltage (V): | 7.3 | 9.0 |

After passage of current, water bubbles are found to be formed all over the area subjected to current passage. The cross-section of the membrane is observed to find that there occurs peel-off exactly at the interface between the laminated films A and B.

EXAMPLES 20–21

Example 19 is repeated except that the reducing agents and the treatment conditions for treatment of one surface having sulfonyl chloride groups are changed as shown in Table 1. The elctrolysis performance, the surface density and the maximum density gradient of carboxylic acid groups are also shown in Table 1.

In any of the membranes after passage of current, there is observed no water bubbles, peel-off or cracks.

TABLE 1

| Example No. | Reducing agent and treatment conditions | Electrolysis performance* After 24 hrs. | Electrolysis performance* After 720 hrs. | Surface density of —COOH (%) | Maximum density gradient (%/μ) |
|---|---|---|---|---|---|
| 20 | 57% hydroiodic acid-propionic acid (15:1, volume ratio) mixture, 72° C., 18 hours | 95/4.8 | 95/4.8 | 100 | 4.5 |
| 21 | 57% hydroiodic acid-caprylic acid (500:1, weight ratio) mixture, 83° C., 20 hours | 94/4.8 | 94/4.8 | 100 | 4.1 |

*Electrolysis performance: Current efficiency (%)/Voltage (V)

EXAMPLE 22

Polymerization is carried out in the same manner as in Example 19 except that $CF_2=CFO(CF_2)_3SC_2H_5$ and

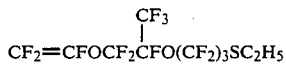
$$CF_2=CFOCF_2CFO(CF_2)_3SC_2H_5$$

are charged at a molar ratio of 4:1. The resultant polymer is treated similarly as described in Example 19. The results obtained are similar to those as reported in Example 19.

EXAMPLE 23

Polymerization is carried out in the same manner as in Example 19 except that the pressure of tetrafluoroethylene is changed to 17 kg/cm². The ion-exchange capacity of a part of the resultant polymer is measured by the same method as in Example 19 to be 0.75 meq/g-dry resin. The ratio of the recurring units in this polymer, i.e.

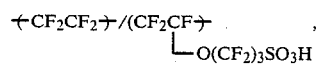

is found to be 10. The above polymer is molded into a film with a thickness of 50μ. This film is called film c. The sulfide type polymer obtained in Example 19 is also molded into a film with a thickness of 100μ. This film is called film d. The film c is placed on the film d and the composite is press molded into a laminated membrane. Then, with the side of the film d downward, said membrane is placed on a fabric made of polytetrafluoroethylene, which is "leno-woven" fabric with a thickness of about 0.15 mm comprising wefts of 400 denier multi-filaments and warps of 200 denier multi-filaments×2. By heating the membrane under vacuo, the fabric is embedded in the film d to reinforce said membrane.

The laminated membrane incorporated with a reinforcing material is subjected to the chlorine treatment similarly as in Example 19 to form a sulfonyl chloride type laminated membrane. Said laminated membrane is treated on the side of the film c with a mixture comprising 57% hydroiodic acid and glacial acetic acid at a volume ratio of 10:1 at 83° C. for 20 hours. After hydrolysis with an alkali, the membrane is further treated with 5% sodium hypochlorite at 90° C. for 16 hours. When the cross-section of the resultant membrane is stained with an aqueous Malachite Green solution adjusted at pH 2, the layer with thickness of 11μ from the surface of the film c is stained in blue, the residual part being stained in yellow. The maximum density gradient of carboxylic acid groups in the layer stained blue is measured to be 4.9%/μ, and the density of carboxylic acid groups on the surface to be 92%.

When the electrolysis performance of the membrane is measured according to the same method as described in Example 19 using 6N alkali concentration, with the side of the film c facing toward the cathode side, there are obtained the following results. The membrane subjected to passage of current is free from water bubbles, peel-off or cracks.

| Current passage time (hrs.): | 24 | 720 |
| --- | --- | --- |
| Current efficiency (%): | 93 | 93 |
| Voltage (V): | 5.5 | 5.5 |

EXAMPLES 24-27

The laminated membrane prepared in Example 23 is treated on the side of the film c with the reducing agents and under the treatment conditions as shown in Table 2, followed by subsequent treatments similarly conducted as in Example 23. The electrolysis performance, the density of carboxylic acid groups on the surface of the film c and the maximum density gradient are set forth in Table 2.

None of these membrane show water bubbles, peeloff or crack after passage cracks after the passage of current.

TABLE 2

| Example No. | Reducing agent and treatment conditions | Electrolysis performance* | | Surface density of carboxylic acid groups (%) | Maximum density gradient (%/μ) |
| --- | --- | --- | --- | --- | --- |
| | | After 24 hours' current passage | After 720 hours' current passage | | |
| 24 | 57% hydroiodic acid-glacial acetic acid (8:1, volume ratio) mixture, 83° C., 15 hours | 92/5.4 | 92/5.4 | 84 | 4.0 |
| 25 | 47% hydrobromic acid-glacial acetic acid (3:1, volume ratio) mixture, 90° C., 16 hours | 91/5.4 | 91/5.4 | 68 | 2.9 |
| 26 | 30% hydrophosphorous acid-propionic acid (3:1, volume ratio) mixture, 90° C., 16 hours | 90/5.3 | 90/5.3 | 54 | 2.4 |
| 27 | 57% hydroiodic acid-perfluorooctanoic acid (500:1, weight ratio) mixture, 72° C., 16 hours | 92/5.4 | 92/5.4 | 81 | 4.2 |

*Electrolysis performance: Current efficiency (%)/Voltage (V)

EXAMPLE 28

In a stainless steel autoclave of 500 cc capacity, there are charged 1,1,2-trichloro-1,2,2-trifluoroethane and $CF_2=CFO(CF_2)_3SO_2C_2H_5$ and perfluoropropionyl peroxide as initiator, and polymerization is carried out at 45° C. under the pressure of tetrafluoroethylene of 15 kg/cm². The resultant polymer is found to contain 4.10% of sulfur, as measured by elemental analysis.

A part of this polymer is hydrolyzed with an alkali containing potassium permanganate and the ion-exchange capacity of the hydrolyzed polymer is measured to be 1.31 meq/g-dry resin.

The above sulfonic type polymer is molded into a membrane with a thickness of 250μ, which is then hydrolyzed with an alkali containing potassium permanganate. Subsequently, said membrane is immersed in a mixture comprising 1:3 (weight ratio) of phosphorus pentachloride and phosphorus oxychloride to be treated at 110° C. for 20 hours. Measurement of the ATR of the resultant membrane gives the result that there appears specific absorption of sulfonyl chloride groups at 1420 cm$^{-1}$.

After one surface of said sulfonyl chloride type membrane is treated with a mixture comprising 15:1 (volume ratio) of hydroiodic acid and propionic acid at 72° C. for 18 hours, the treated membrane is subjected to hydrolysis treatment with an alkali, followed further by treatment with an aqueous 5% sodium hypochlorite solution at 90° C. for 16 hours. When the cross-section of the membrane is stained with an aqueous Malachite Green solution, the layer with a thickness of 11μ from one surface is found to be stained in blue, while the remaining portion is stained in yellow. The surface density and the maximum density gradient of carboxylic acid groups in the layer stained in blue are found to be 100% and 5.1%/μ, respectively.

EXAMPLES 29-32

One surface of the sulfonyl chloride type membrane prepared in Example 28 is treated similarly as in Example 28 using various reducing agents and treatment conditions as shown in Table 3. The density of carboxylic acid groups on the surface of the membrane and the maximum density gradient of carboxylic acid groups are also shown for each membrane obtained in Table 3.

TABLE 3

| Example No. | Reducing agent and treatment conditions | Surface density of carboxylic acid groups (%) | Maximum density gradient of carboxylic acid groups (%/μ) |
|---|---|---|---|
| 29 | 47% hydrobromic acid-caprylic acid (500:1, weight ratio) mixture, 90° C., 30 hrs. | 69 | 4.9 |
| 30 | 30% hypophosphorous acid-glacial acetic acid (5:1, volume ratio) mixture, 90° C., 16 hrs. | 60 | 3.0 |
| 31 | 30% hypophosphorous acid perfluorooctanoic acid (500:1, weight ratio) mixture, 83° C. 24 hrs. | 75 | 4.9 |
| 32 | 57% hydroiodic acid-perfluoroheptane-sulfonic acid (550:1, weight ratio) mixture, 90° C., 16 hrs. | 94 | 4.6 |

EXAMPLE 33

The copolymer prepared according to the polymerization method as described in Example 19 is extruded into a strand, which is then cut into a granular resin of 1 mm in size by means of a pelletizer.

The functional groups contained in said resin are converted to sulfonyl chloride groups by the method as described in Example 19, followed by hydrolysis to be converted to sulfonic acid groups. Then, the ion-exchange capacity of the resin is measured to be 1.3 meq/g-dry resin.

EXAMPLE 34

An emulsion is formed in a stainless steel autoclave of 300 cc capacity by charging 10 g of CF$_2$=CFO(CF$_2$)$_3$SCH$_3$, 1.0 g of sodium hydrogen phosphate, 45 cc of purified water and 0.45 g of ammonium perfluorooctanoate. Then, 5 cc of 0.62% aqueous ammonium persulfate solution is added to the emulsion and polymerization is carried out, while maintaining the temperature at 40° C., under the pressure of tetrafluoroethylene of 13 kg/cm$^2$, whereby the pressure of tetrafluoroethylene is controlled so as to keep constant the polymerization rate. The resultant polymer is found to contain 3.50 wt.% of sulfur by elemental analysis. This polymer is press molded into a thin film at 280° C. and subjected to measurement of ATR, whereby there is observed absorption of methyl groups at 3000 cm$^{-1}$.

The above polymer is molded into a membrane with a thickness of 150μ, which is in turn treated with chlorine gas at 120° C. for 20 hours. Measurement of the ATR of the membrane gives the result that the absorption of methyl groups at around 3000 cm$^{-1}$ has vanished. Furthermore, said membrane is treated with a liquid saturated with chlorine, comprising a mixture of perfluorobutyric acid and water (2:1, volume ratio) having dissolved chlorine therein, at 100° C. for 48 hours. Measurement of the ATR of said membrane shows that there appears absorption of sulfonyl chloride groups at around 1420 cm$^{-1}$. Ion-exchange capacity of said membrane is determined after hydrolysis of a part thereof with an alkali to be 1.04 meq/g-dry resin. The ratio of the recurring units of the membrane, i.e.

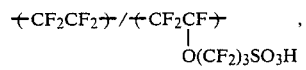

is found to be 6.7.

One surface of the above sulfonyl chloride type membrane is treated with a mixture comprising 57% hydroiodic acid and acetic acid at 30:1 (volume ratio) at 72° C. for 16 hours, followed by hydrolysis with an alkali, and further treated with an aqueous 5% sodium hypochlorite solution at 90° C. for 16 hours. By staining the cross-section of one surface of the membrane, the layer on one side of the membrane with a thickness of 12μ is found to be stained in blue, while the remaining portion is stained in yellow. Electrolysis performance is measured under the same conditions as used in Example 19, with the surface stained in blue of the membrane facing toward the cathode side, to give the result as shown below. The density of carboxylic acid groups and the maximum density gradient are also measured to give the following values.

| Electrolysis performance | | | |
|---|---|---|---|
| After 24 hours' current passage | After 720 hours' current passage | Surface carboxylic acid group density (%) | Maximum density gradient (%/μ) |
| 95%/5.0 | 95%/5.0 | 100 | 4.2 |

EXAMPLE 35

An emulsion is formed in a stainless steel autoclave of 300 cc capacity by charging 10 g of CF$_2$=CFO(CF$_2$)$_3$SC$_2$H$_5$, 0.1 g of ammonium persulfate and water, using ammonium perfluorooctanoate as emulsifier. Tetrafluoroethylene is pressurized into the autoclave at 15 kg/cm$^2$ and polymerization is carried out at 50° C. by adding sodium hydrogen sulfite as co-catalyst. The resultant polymer is found to contain 4.23 wt.% of sulfur by elemental analysis. This polymer is molded into a membrane with a thickness of 250μ, which is in turn treated with chlorine gas at 120° C. for 20 hours, followed further by treatment with a saturated aqueous chlorine solution at 83° C. for 20 hours. The ATR of this membrane is measured, whereby the absorption appearing at around 3000 cm$^{-1}$ before chlorine treatment is found to have vanished and instead there appears absorption of sulfonyl chloride groups at around 1420 cm$^{-1}$. Ion-exchange capacity of said membrane is measured after hydrolysis with an alkali to be 1.3 meq/g-dry resin, indicating that the ratio of the recurring units, i.e.

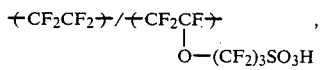

is 4.4.

The electrolysis performance of said membrane is measured according to the following method.

There is used an electrolytic cell comprising the anode compartment and the cathode compartment separated by said membrane with a current passage area of 0.06 dm$^2$ (2 cm×3 cm) and said membrane is assembled in the cell. As the anode, a dimensionally stable electrode is used and as the cathode an iron plate. A saturated aqueous sodium chloride solution is charged into the anode compartment and adjusted at pH 3 by adding hydrochloric acid thereto. While 13N aqueous caustic soda solution is circulated to the cathode compartment, water is added thereto in order to maintain the concentration at a constant value.

While maintaining the temperatures in both the anode compartment and the cathode compartment at 110° C., current is passed at the current density of 120 A/dm$^2$. The current efficiency is calculated by dividing the amount of caustic soda formed in the cathode compartment by the theoretical amount calculated from the quantity of current passed to be 65%. After current is passed for 700 hours, there is observed no physical damage on the membrane such as bubble formation, cracks or peel-off.

EXAMPLE 36

An emulsion is formed by charging 10 g of CF$_2$=CFO(CF$_2$)$_3$SCH$_3$, 1.0 g of sodium hydrogen phosphate, 45 cc of purified water and 0.45 g of ammonium perfluorooctanoate in a stainless steel autoclave of 300 cc capacity. Then, 5 cc of an aqueous 0.62% ammonium persulfate solution is added to the mixture, and polymerization is conducted under the pressure of tetrafluoroethylene of 13 kg/cm$^2$, while maintaining the temperature at 40° C. During the polymerization, the pressure of tetrafluoroethylene is controlled so as to keep constant the rate of polymerization. The resultant polymer is found to contain 3.5 wt.% of sulfur by elemental anlaysis. This polymer is press molded at 280° C. into a thin film, which is subjected to measurement of ATR, whereby it is found that there is observed absorption of methyl groups at around 3000 cm$^{-1}$.

A membrane with a thickness of 150μ prepared by molding of the above polymer is treated with chlorine gas at 120° C. for 20 hours, whereby absorption of methyl groups at around 3000 cm$^{-1}$ is found to have vanished as measured by the ATR of the membrane. Further, said membrane is treated with a liquid saturated with chlorine, comprising a mixture of perfluorobutyric acid and water at 2:1 (volume ratio) having dissolved chlorine therein, at 100° C. for 48 hours. Measurement of the ATR of the resultant membrane gives the result that there appears absorption of sulfonyl groups at around 1420 cm$^{-1}$. The ion-exchange capacity of said membrane is measured after hydrolysis of said membrane with an alkali to be 1.04 meq/g-dry resin, thus giving the ratio of the recurring units of the membrane, i.e.

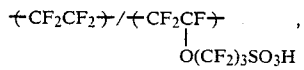

of 6.7.

EXAMPLE 37

The polymer prepared in Example 19 is molded into a film with a thickness of 200μ. A fabric made of polytetrafluoroethylene fibers is embedded in this film according to the following method. The device used in this embedding procedure comprises two aluminum plates, each being provided on the upper surface by mechanical working with a series of grooves so as to create a pressure difference across the upper surface of the plate. The pressure difference is applied through the hole bored through the side surface of the plate, said hole being connected to the grooves on the upper surface of the plate. On this plate is placed a 60-mesh wire-screen so that the pressure difference may be applied on every point on the upper surface. A sheet of asbestos paper is placed on the upper surface of the wire-screen, and on said sheet is superposed a "leon-woven" fabric with a thickness of about 0.15 mm made of polytetrafluoroethylene fibers comprising, each 25 per inch, 400 denier multi-filaments as weft and 200 denier multifilaments×2 as warp. On said fabric is further placed the above film. The size of the film is made slightly larger than the other components and the marginals of the sheets of the fluorinated polymer are fastened onto the aluminum plates with a tape, thus forming an airtight package.

The embedding device is placed between the elctrically heated hot plates, whereby the hot plate contacted with the aluminum plate is maintained at 300° C. and the hot plate contacted with the film at 180° C. for 5 minutes. Then, through the hole on the side surface of the aluminum plate, evacuation is effected to provide a 100 mm Hg pressure difference. Under such conditions, the whole composite is left to stand for 3 minutes. The temperature of the hot plates is then cooled to room temperature and the pressure difference is removed. By observation of the cross-section of the film, the fabric is completely embedded within the film.

When the thus prepared membrane is treated with chlorine gas and subsequent treatments as described in Example 19, there is obtained a membrane having similar current efficiency according to the same evaluation test of electrolysis performance as described therein.

We claim:

1. A fluorinated acid fluoride represented by the formula:

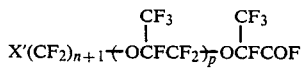

wherein X' is —SR or —SO$_2$R, R is C$_1$-C$_{10}$ alkyl, C$_1$-C$_{10}$ perfluoroalkyl, an aryl or chlorine, n is an integer of 2 to 4 and p is an integer of 0 to 50.

2. A fluorinated acid fluoride according to claim 1, wherein p is 0 and n is 2.

3. A fluorinated acid fluoride according to claim 2, wherein R is —CH$_3$ or —C$_2$H$_5$.

4. A fluorinated acid fluoride according to claim 1, wherein p is 1 and n is 2.

5. A fluorinated acid fluoride according to claim 4, wherein X' is —SC$_2$H$_5$.

* * * * *